US012779213B2

(12) United States Patent
Wolf, II

(10) Patent No.: US 12,779,213 B2
(45) Date of Patent: Nov. 3, 2026

(54) SYSTEM AND METHOD FOR PERCUTANEOUS LEAD ANCHORING

(71) Applicant: Wavegate Corporation, Lake Charles, LA (US)

(72) Inventor: Erich W. Wolf, II, Lake Charles, LA (US)

(73) Assignee: Wavegate Corporation, Lake Charles, LA (US)

( * ) Notice: Subject to any disclaimer, the term of this patent is extended or adjusted under 35 U.S.C. 154(b) by 887 days.

(21) Appl. No.: 17/443,174

(22) Filed: Jul. 21, 2021

(65) Prior Publication Data

US 2022/0023620 A1 Jan. 27, 2022

Related U.S. Application Data

(60) Provisional application No. 62/705,893, filed on Jul. 21, 2020.

(51) Int. Cl.
*A61N 1/05* (2006.01)

(52) U.S. Cl.
CPC .................................. *A61N 1/0558* (2013.01)

(58) Field of Classification Search
CPC ................ A61N 1/0558; A61N 1/0551; A61N 1/36017; A61N 1/3752; A61N 1/3756; A61N 1/37518; A61N 1/057; A61N 1/059; A61N 1/056; A61N 1/0573; A61N 1/0587; A61N 1/3956; A61N 1/39622; A61N 1/0565; A61B 17/3468; A61B 17/0401; A61B 2017/0409; A61B 2017/0412; A61B 2017/0414; A61B 2017/0427; A61B 2017/0446; A61B 2017/045;

(Continued)

(56) References Cited

U.S. PATENT DOCUMENTS 5,562,670 A 10/1996 Branemark et al.
6,356,792 B1 3/2002 Errico et al.

(Continued)

FOREIGN PATENT DOCUMENTS

DE 3942735 A1 6/1991
WO 2011150480 A1 12/2011

OTHER PUBLICATIONS

Holly, L.T., et al, “Percutaneous Placement of Posterior Cervical Screws Using Three-Dimensional Fluoroscopy,” Spine (Mar. 1, 2006) 31(5):536-540.

(Continued)

*Primary Examiner* — Tan-Uyen T Ho
*Assistant Examiner* — Bridget E. Rabaglia
(74) *Attorney, Agent, or Firm* — Schultz & Associates, P.C.

(57) ABSTRACT

The invention described is comprised of a system and method for rapid fixation of a lead anchor. The system includes a lead anchor and insertion device. The insertion device houses a lead anchor. A lead is threaded through the insertion device and the device is depressed against the fascia to insert the lead anchor and fix the lead in the desired position. This method produces repeatable amount of lead body compression grasp force, and controlled bend radius. This results in rapid lead anchoring, lowers the risk of lead migration, prevents mechanical damage to the lead due to over-compression and eliminates the need for tying a suture.

18 Claims, 25 Drawing Sheets

(58) Field of Classification Search
CPC . A61B 2017/0451; A61B 90/11; A61B 18/14; A61B 5/0215; A61B 2017/1205; A61B 2018/00351; A61B 2018/00357; A61B 2090/103
USPC .......................................................... 606/129
See application file for complete search history.

(56) References Cited

U.S. PATENT DOCUMENTS

| | | | |
|---|---|---|---|
| 6,778,861 | B1 | 8/2004 | Liebrecht et al. |
| 7,657,308 | B2 | 2/2010 | Miles et al. |
| 8,070,785 | B2 | 12/2011 | Biscup |
| 8,075,630 | B2 | 12/2011 | Ricci et al. |
| 8,348,983 | B2 | 1/2013 | Neubardt |
| 8,380,319 | B2 | 2/2013 | Berger |
| 8,486,119 | B2 | 7/2013 | Bourlion |
| 8,600,495 | B2 | 12/2013 | Gielen et al. |
| 8,738,144 | B2 | 5/2014 | Schneider |
| 9,205,260 | B2 | 12/2015 | Kim et al. |
| 9,232,906 | B2 | 1/2016 | Wolf |
| 9,259,248 | B2 | 2/2016 | Leuthardt et al. |
| 9,387,319 | B2 | 7/2016 | Pianca |
| 9,439,694 | B2 | 9/2016 | Kraus et al. |
| 9,474,900 | B2 | 10/2016 | Kraus |
| 9,579,222 | B2 | 2/2017 | Branemark et al. |
| 9,737,233 | B2 | 8/2017 | Londot |
| 9,883,898 | B2 | 2/2018 | Smith |
| 10,143,848 | B2 | 12/2018 | Datta |
| 10,154,866 | B2 | 12/2018 | Kim |
| 10,172,658 | B2 | 1/2019 | Kim |
| 2004/0243207 | A1 | 12/2004 | Olson et al. |
| 2010/0036467 | A1 | 2/2010 | Kraus et al. |
| 2010/0106198 | A1 | 4/2010 | Adcox et al. |
| 2010/0298886 | A1 | 11/2010 | Kraus et al. |
| 2018/0093094 | A1* | 4/2018 | Wolf, II ............... A61N 1/0558 |
| 2018/0132961 | A1* | 5/2018 | van Venrooij ......... A61B 90/10 |

OTHER PUBLICATIONS

Sairyo, K., et al, “Minimally invasive technique for direct repair of pars interarticularis defects in adults using a percutaneous pedicle screw and hook-rod system,” Journal of Neurosurgery: Spine (May 2009) 10(5):492-495.

North, R.A., et al, “Spinal Cord Stimulation Electrode Design: A Prospective, Randomized, Controlled Trial Comparing Percutaneous with Laminectomy Electrodes: Part II—Clinical Outcomes,” Neurosurgery (Nov. 1, 2005) 57(5):990-996.

* cited by examiner

SYSTEM AND METHOD FOR PERCUTANEOUS LEAD ANCHORING

CROSS-REFERENCE TO RELATED APPLICATIONS

This application claims priority benefit from U.S. Provisional Application No. 62/705,893 filed on Jul. 21, 2020. The patent application identified above is incorporated here by reference in its entirety to provide continuity of disclosure.

FIELD OF THE INVENTION

The present invention relates to insertion and anchoring for spinal cord stimulator percutaneous leads.

BACKGROUND OF THE INVENTION

Mechanical compression or injury to spinal nerves with resulting radicular pain can develop in response to a variety of conditions, including spondylolisthesis, osteoarthritis, and degenerative disc disease, among others. Nerve root irritation can also result in numerous symptoms aside from the radicular pain, including both sensory and motor deficiencies, such as numbness of the extremities, weakness, and difficulty with or loss of dexterity and muscle control.

FIG. 1A shows a drawing of the human spine including spinal column 10. Spinal column 10 is comprised of a number of vertebrae, categorized into four sections, the lumbar vertebrae 12, the thoracic vertebrae 14, the cervical vertebrae 16 and the sacral vertebrae 18. Starting at the top of the spinal column, cervical vertebrae 16 include the 1st cervical vertebra (C1) through 7th cervical vertebra (C7). Just below the 7th cervical vertebra is the first of twelve thoracic vertebrae 14 including the 1st thoracic vertebra (T1) through 12th thoracic vertebra (T12). Just below the 12th thoracic vertebrae 14, are five lumbar vertebrae 12 including the 1st lumbar vertebra (L1) through 5th lumbar vertebra (L5). The 5th lumbar vertebra is attached to the sacral vertebrae 18 (S1 to S5), the sacral vertebrae 18 being naturally fused together in the adult.

FIG. 1B shows an axial view of representative lumbar vertebrae 12. Representative lumbar vertebra 20 has a number of features which are shared with the thoracic vertebrae 14 and cervical vertebrae 16, although the feature thicknesses and shapes may vary. The thick oval segment of bone forming the anterior aspect of lumbar vertebra 20 is the vertebral body 21. Vertebral body 21 is attached to a bony vertebral arch 22 through which the neural elements run. Vertebral arch 22, forming the posterior of lumbar vertebra 20, is comprised of two pedicles 23, which are short stout processes that extend from the sides of vertebral body 21, and two laminae 25, the broad flat plates that project from pedicles 23 and join in a triangle to form a hollow archway, the spinal canal 27. Spinous process 26 protrudes from the junction of laminae 25. The pars interarticularis 28 is the thin wall of bone that is part of the lamina and is located between the superior articular process and inferior articular process. Transverse processes 24 project from the junction of pedicles 23 and laminae 25. The structures of the vertebral arch protect the spinal cord and/or spinal nerves that run through the spinal canal.

In FIG. 1C, a representative drawing of the human back anatomy is shown.

Lumbar vertebrae 32, thoracic vertebrae 34, cervical vertebrae 36 and sacral vertebrae 38 are shown relative to body 30. The back is further comprised of muscles, tendons, and fascia. Fascia is a layer of fibrous connective tissue that can interpenetrate and surround muscle tissues.

Nuchal ligament 40 extends from external occipital protuberance 33 of skull 35 to the spinous process of C7 in cervical vertebrae 36 where it connects to deep fascia 44 of the back. Deep fascia 44 attaches medially to the nuchal ligament. Deep fascia 44 is further connected to the tips of the spinous processes of the vertebrae, the supraspinous ligament, and thoracolumbar fascia 48 at the thoracic and lumbar regions.

Thoracolumbar fascia 48 is roughly diamond-shaped and begins at the deep fascia in the thoracic region and terminates at median crest 52 of the sacrum. The thoracolumbar fascia 48 extends laterally from the spinous processes of the vertebral column forming a thin covering for the deep muscles in the thoracic region and a strong thick covering for muscles in the lumbar region where it is widest.

Back muscles are generally grouped in two general categories, extrinsic and intrinsic. Extrinsic back muscles lie superficially on the back and are generally associated with arm movement rather than movement of the vertebral column. Extrinsic muscles include trapezius 42, latissimus dorsi 46, levator scapulae, the rhomboid muscles, and the serratus posterior muscles. Thoracolumbar fascia 48 attaches to trapezius muscle 42, latissimus dorsi 46, gluteus maximus 50, and the hamstrings group of muscles.

Intrinsic muscles, which are responsible for movement of the vertebral column, are located deep in the body beneath thoracolumbar fascia 48. Intrinsic muscles (not shown) include the splenius muscles, erector spinae muscles, transversospinal muscles, and interspinales and intertransversarii muscles. Thoracolumbar fascia 48 surrounds the intrinsic muscles of the back and lumbar regions and divides the muscles into compartments. It also houses the quadratus lumborum, transverseospinalis, spinal erectors and multifidus muscles, and corresponding tendons.

Patients experiencing chronic spinal or appendicular pain are frequently treated using spinal cord stimulation which delivers electrical pulses to the dorsal aspect of the spinal cord, via an electrode array, to block the pain from being perceived by the brain.

To achieve this, an electrode array is implanted into the dorsal epidural space and connected to an implanted pulse generator. The electrode array resides at the distal end of a lead, which is comprised of a slender multi-lumen cable, roughly 1.4 mm diameter with the outer lead body material composed of Pellethane 55-D or similar material. The electrodes are electrically connected to a set of electrical contacts on the proximal end of the lead. The proximal lead end connects to the implanted pulse generator.

Leads are placed under fluoroscopic guidance via a Tuohy needle (typically 14-gauge), which is placed into the dorsal epidural space using loss-of-resistance or Seldinger technique. After achieving adequate lead placement, the Tuohy needle is withdrawn, leaving the percutaneous lead in situ.

Typically, percutaneous leads are placed such that they enter the thoracolumbar fascia at the mid-lumbar region. Leads are typically anchored to the thoracolumbar fascia to achieve some degree of positional stability.

Despite anchoring, electrode arrays and leads are still prone to migration, which both diminishes the efficacy of the stimulation technique and can cause other complications necessitating surgical correction of the migration or removal of the electrode array. The anchoring process may be complicated by the depth of the fascia relative to the skin, particularly with relatively small incisions, and is dependent upon how secure the ligature engages the lead and anchoring sleeve.

One known method of lead fixation utilizes a cylindrical sleeve of polymeric material (e.g., Silastic) which is slipped over the lead down to the site where the lead exits the fascia. A permanent suture is then placed through the fascia and tied around the lead anchor and the lead is cinched in place. If the suture is not cinched down adequately tightly then the lead is susceptible to pull-out with the attendant risk of lead migration complications. If the suture is cinched too tightly, this can focally compress the lead conductors and result in premature failure. This is also a risk if the lead contains an integrated optical fiber such as in optical reflectometry applications.

Similarly, the problem of electrode array migration has been addressed by other prior art techniques, but has not been adequately resolved and migration remains a problem.

U.S. Publication No. 2017/0021180 to Datta discloses a method for implantation of a neural stimulator comprised of electrodes attached to a generator. The electrodes are connected to the generator via a subcutaneous lead with connector plugs. However, the method anchors the electrode to the soft tissue near the targeted nerve, which leaves the electrode susceptible to migration.

U.S. Publication No. 2016/0199112 to Kim discloses a medical insertion apparatus comprised of a screw nail body to be implanted in a boney structure that includes an electrode. The screw nail body includes an electrode connected to a lead which runs along the length of the screw nail body either inside a cavity or along the outside edge, or a combination thereof. The position of the electrode is fixed at the terminal end of the screw nail body, requiring the screw nail body to be located immediately peripheral to the targeted nerve, which is not always possible when targeting the spinal cord. Furthermore, the screw nail body must be seated perpendicularly to the surrounding bone, prohibiting an electrode position parallel to the spinal cord. Alternatively, using an array of electrodes that extends beyond the tip of the screw nail body leaves no way to position the array precisely.

U.S. Pat. No. 6,356,792 to Errico, et al. discloses an assembly for securing an electrode inside a patient's skull. A skull port member is affixed to the skull. An electrode is placed inside the skull and the connecting lead is run through the skull port member. The electrode is secured by a mechanism that seats in the skull port member and crimps the connecting lead. However, the electrode is susceptible to movement when the operator inserts the lead-locking mechanism into the skull port member and crimps the connecting lead. The nature of the mechanism also limits the possible materials and possible sizes of the assembly, as thinner and lighter materials in the connecting lead would be likely to break when crimped in place by the lead locking mechanism. Furthermore, the design is ill-suited for use in the spine, as there is no way to position the electrode perpendicular to the direction of the skull port member, which is desirable for stimulation of spinal nerves.

U.S. Pat. No. 9,737,233 to Londot discloses an assembly having a pedicle screw with an electrically-conductive longitudinal member that is used to propagate a signal along the exterior of the pedicle screw. However, the assembly does not allow for placement of the electrode beyond the pedicle screw and limits locations to which electrical stimulation can be applied.

U.S. Pat. No. 9,579,222 to Branemark, et al. discloses a percutaneous gateway for transmission of signals from a patient's nervous system to a robotic prosthesis. The system discloses an apparatus for mounting a prosthesis and preserving the percutaneous transmission of signals with appropriate seals to prevent infection after long-term use, as well as use with stimulating electrodes that may optionally be implanted. However, the system does not disclose a method for locating the electrodes relative to targeted nerves, anchoring the position of the electrodes, or implantation in the spine.

Hence, there remains a need for an electrode array and implantation technique that can reliably and effectively anchor the lead in place to reduce or eliminate future migration.

SUMMARY OF THE INVENTION

The invention described is comprised of a system and method for rapid fixation of a lead anchor. The system includes a lead anchor and insertion device. The insertion device houses a lead anchor. A lead is threaded through the insertion device and the device is depressed against the fascia to insert the lead anchor and fix the lead in the desired position. This method produces repeatable amount of lead body compression grasp force, and controlled bend radius. This results in rapid lead anchoring, lowers the risk of lead migration, prevents mechanical damage to the lead due to over-compression and eliminates the need for tying a suture.

BRIEF DESCRIPTION OF THE DRAWINGS

In the detailed description of the preferred embodiments presented below, reference is made to the accompanying drawings.

DETAILED DESCRIPTION OF THE INVENTION

In the description that follows, like parts are marked throughout the specification and figures with the same numerals, respectively. The figures are not necessarily drawn to scale and may be shown in exaggerated or generalized form in the interest of clarity and conciseness.

Figure 1A:
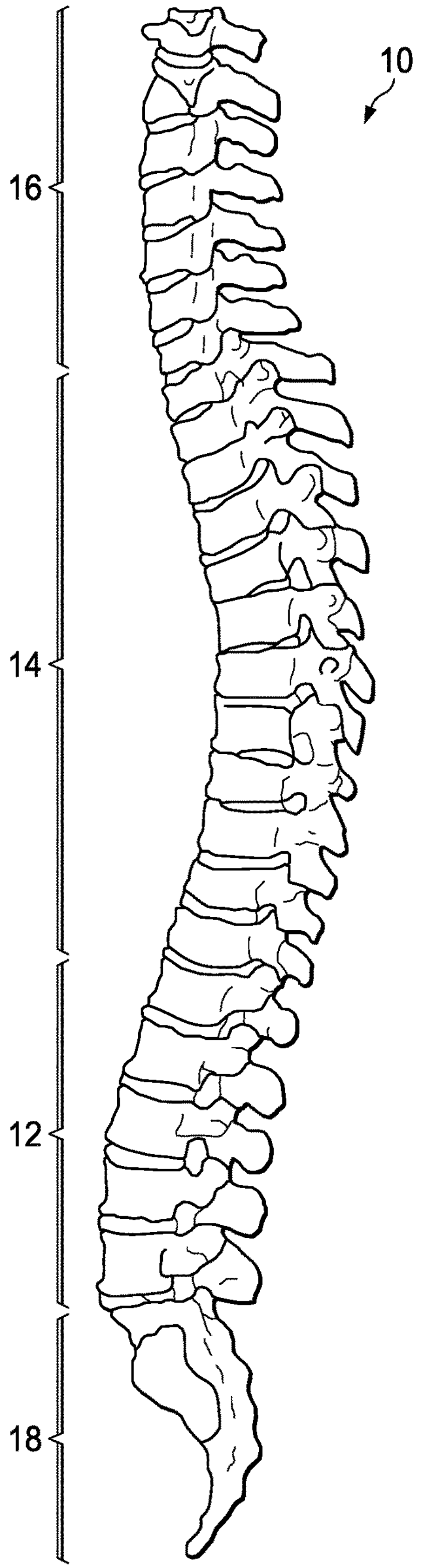
FIG. 1A is a median view of the human spine, showing the different types of vertebrae and their approximate location.
Figure 1B:
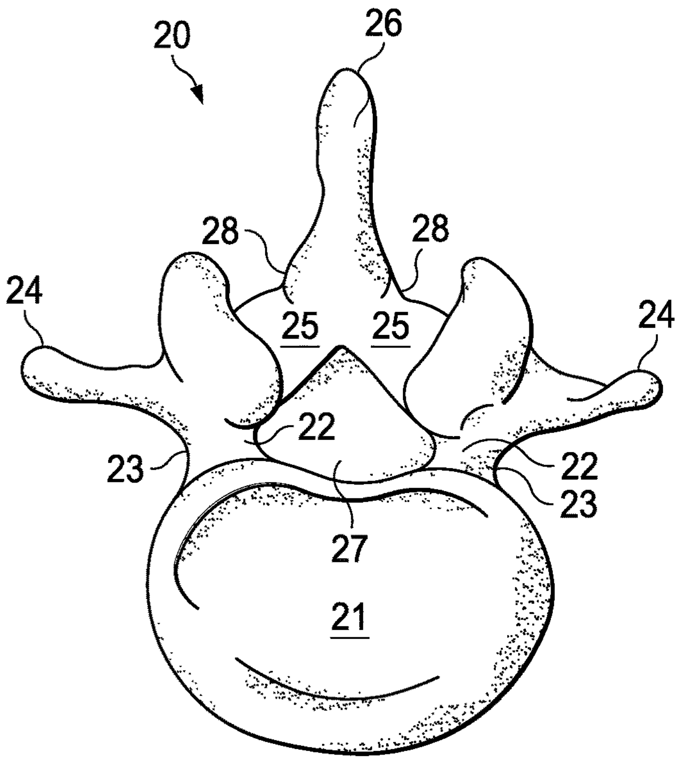
FIG. 1B is an axial view of the lumbar vertebra, showing the various bone features.
Figure 1C:
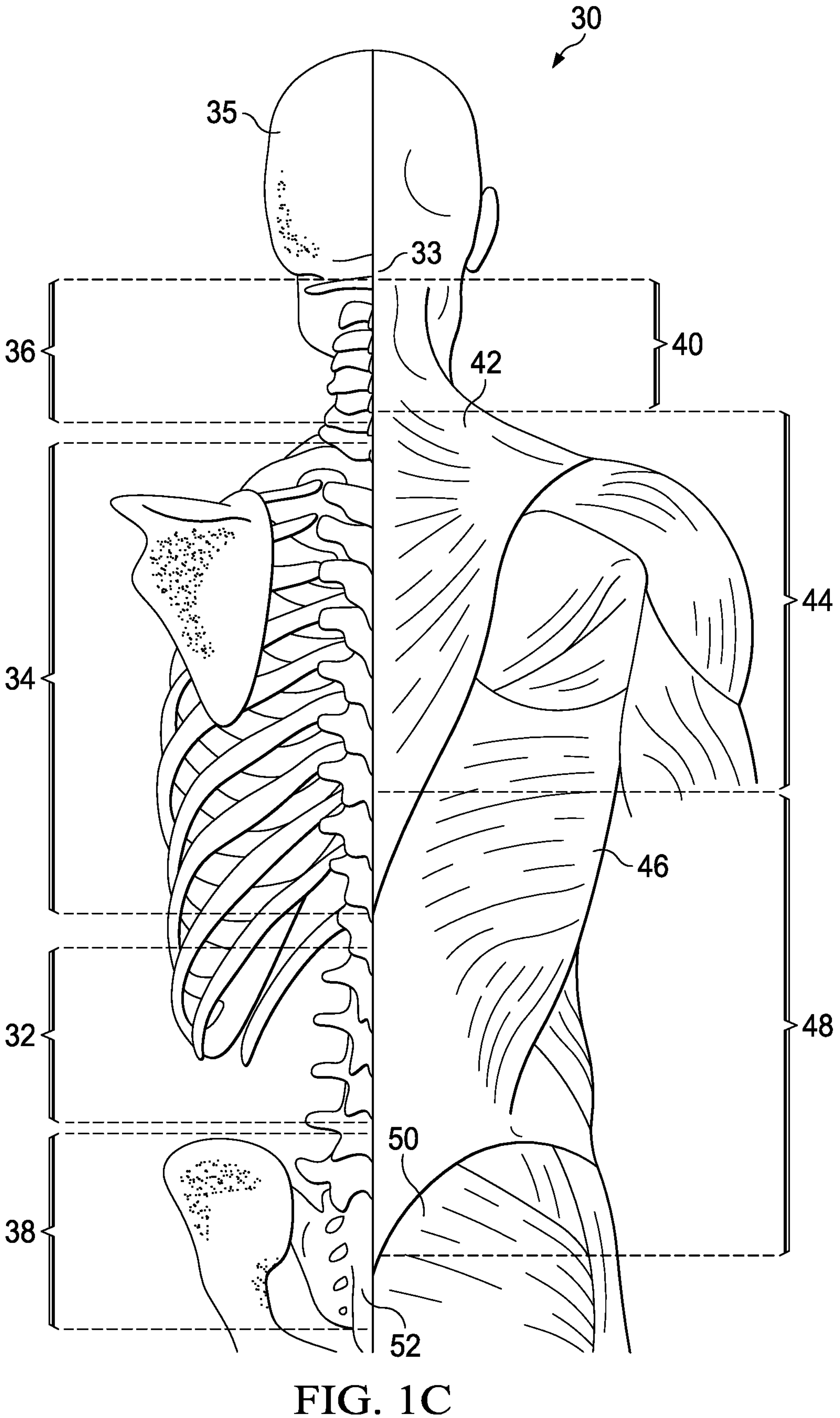
FIG. 1C is a posterior view of the human back, showing the different types of bones, superficial muscles and fascia, and their approximate locations.
Figure 2A:
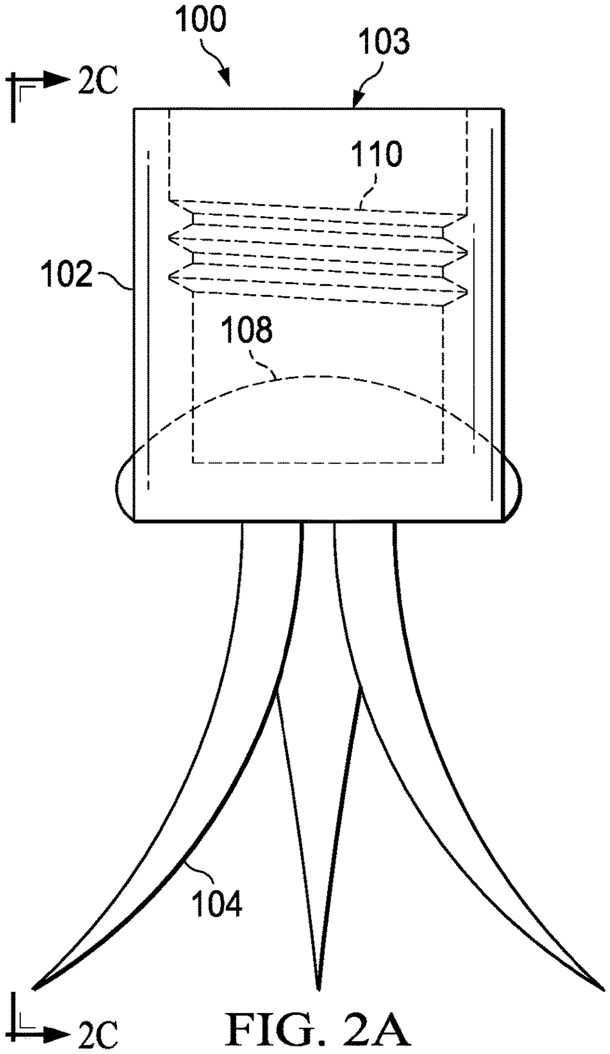
FIG. 2A is a side view of a preferred embodiment of a lead anchor.
Figure 2C:
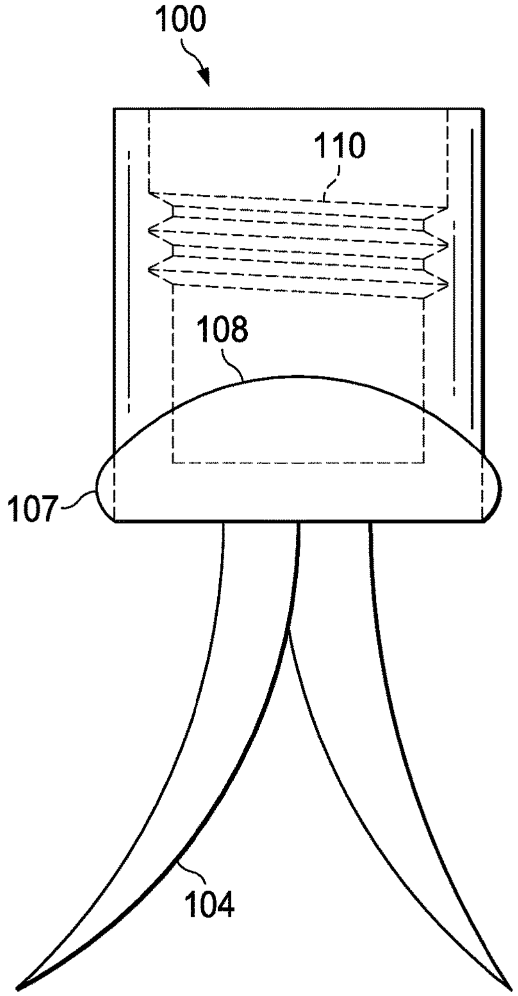
FIG. 2C is a cross-sectional side view of a preferred embodiment of a lead anchor.
Figure 2B:
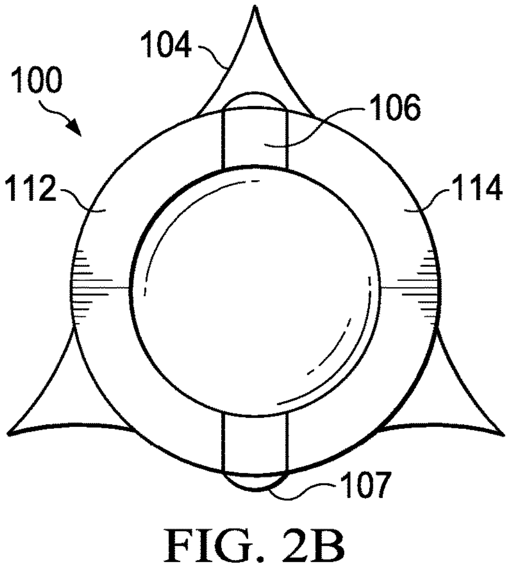
FIG. 2B is a top view of a preferred embodiment of a lead anchor.

Referring then to FIGS. 2A, 2B and 2C, a preferred embodiment of percutaneous lead anchor 100 will be described.

Percutaneous lead anchor 100 is composed of anchor body 102 and tines 104. In a preferred embodiment, three or more tines 104 emanate from the bottom of anchor body 102. The tines are generally a curved triangular shape which are sharp at the tip and engage the fascia. Tines 104 may be composed of Nickel-Titanium "memory metal" alloy or alternatively, a biocompatible polymer such as medical grade nylon 12, by which the tines can be deformed to a straightened configuration by squeezing but then return to a deployed position upon release. Thus, tines 104 may be pushed into the fascia in a straightened position and spontaneously deploy into a curved position fixing anchor body 102 rigidly against the fascia.

Anchor body 102 is comprised of generally a hollow cylindrical shape comprised of wall 112, wall 114, bevel 108, and opening 103. Walls 112 and 114 are semicylinders and form lead channel 106. Bevel 108 is located at the bottom of the anchor body and is a convex semispherical shape. In an alternate embodiment the bevel may be concave or consist of an alternate shape. Opening 103 is located at the top of the anchor body diametrically opposed to bevel 108.

Anchor body 102 includes anchor threads 110 on the inside of walls 112 and 114. In a preferred embodiment, the anchor body is composed of a slightly malleable material such as medical grade nylon 12 which allows the anchor threads to deform to accept endcap threads, as will be further described.

Anchor body 102 is further comprised of external ridges 107 adjacent to lead channel 106.

Figure 2D:
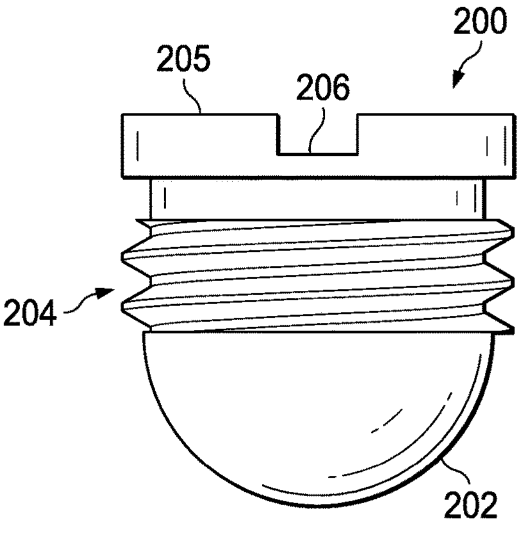
FIG. 2D is a side view of a preferred embodiment of an endcap for a lead anchor.

Referring then to FIG. 2D, endcap 200 for percutaneous lead anchor 100 is described.

Endcap 200 is comprised of nylon 12, or similarly malleable material. Alternatively, the endcap may be comprised of polyether ether ketone (PEEK). Endcap 200 is generally cylindrical in shape and is comprised of bevel 202, endcap threads 204 and top 205. Bevel 202 is semispherical in shape and will be placed in opposition to bevel 108.

The diameter of top 205 is slightly smaller than the diameter of opening 103. Top 205 includes slot 206. The slot may be rectangular, or a cross shape and may be engaged by a screwdriver for removal.

Endcap threads 204 are designed to engage with anchor threads 110. The anchor threads deform to accept the endcap threads via a press fit, similar to a zip tie. The mating of the threads is designed so that the threads engage under compression and may be disengaged by rotating endcap 200, typically counterclockwise, via slot 206.

Figure 3:
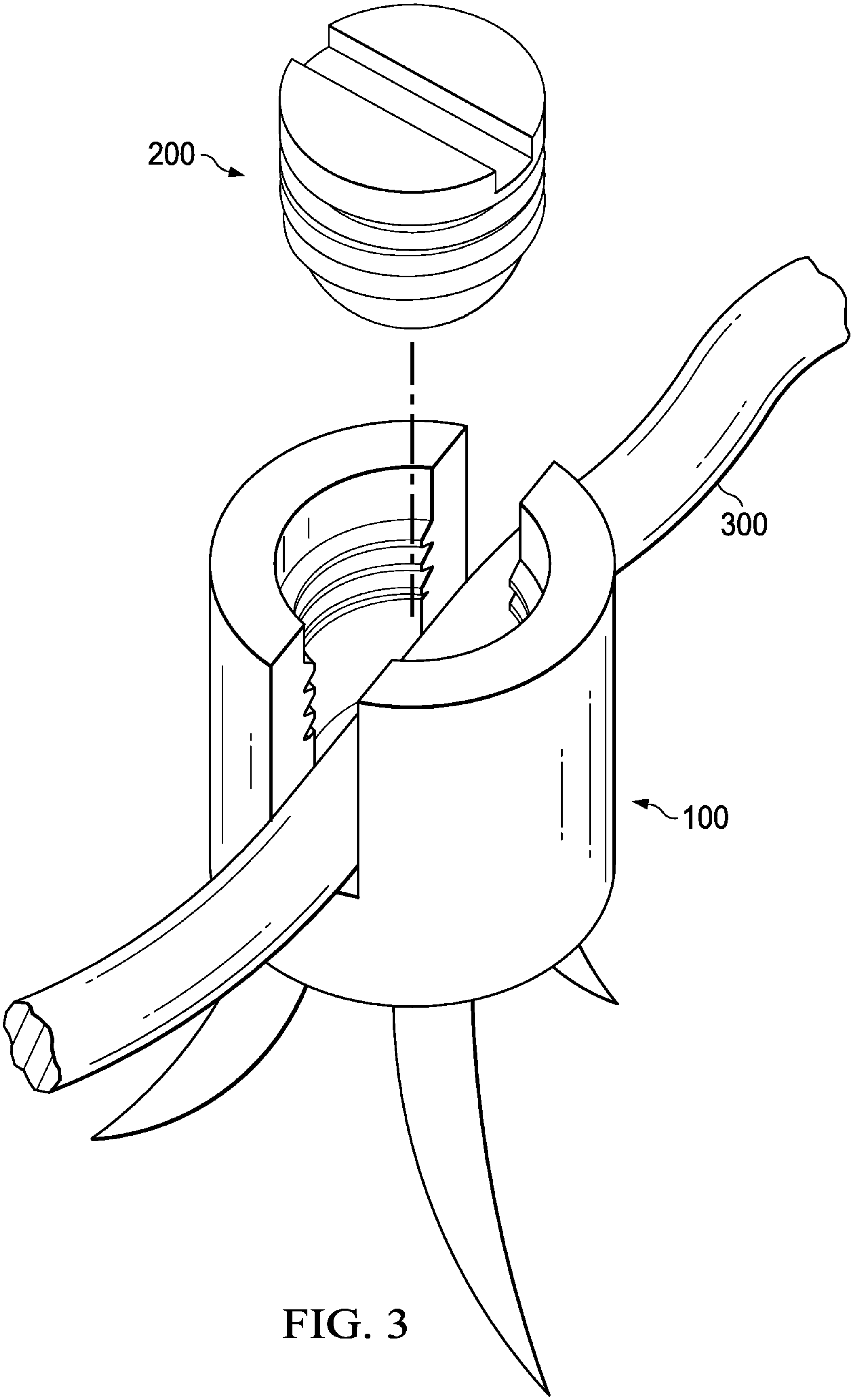
FIG. 3 is an exploded isometric view of a lead anchor and endcap with a percutaneous lead.

Referring then to FIG. 3, percutaneous lead anchor 100 is shown with endcap 200.

Percutaneous lead body 300 is be placed through lead channel 106 then locked into place with endcap 200. Percutaneous lead body 300 is pinched with a controlled force by the apposition of anchor bevel 108 against endcap bevel 202. This compression is designed to limit the lead bending radius of curvature to roughly 5 mm.

Referring then to FIGS. 4A, 4B, 4C, 4D and 4E, anchor deployment tool 400 is described. Anchor deployment tool 400 provides a rapid method of deploying the anchor into the fascia, engaging the lead body, and attaching the endcap.

Anchor deployment tool 400 is comprised of tube 404 and plunger 406. Tube 404 is generally a hollow cylindrical shape with frustoconical taper 403 connecting tip 402 at one end. Tip 402 is a similarly hollow cylinder coaxial with tube 404. Tip 402 is further comprised of notches 418 on the external surface.

Tube 404 includes longitudinal slots 420. Percutaneous lead body 300 is threaded through slots 420.

Tube 404 is further comprised of notches 424, spline guides 422, and detent blocking ring 410. Notches 424 are located on the external surface of tube 404, diametrically opposed to the tip. Spline guides 422 are longitudinally oriented on the inner surface of tube 404, adjacent notches 424. Detent blocking ring 410 is latitudinally oriented and located on the inner surface towards the end of tube 404.

Plunger 406 is comprised of plunger body 407, knurled knob 428, and flash 408. Flash 408 is a thin extension which connects plunger 406 to endcap 200. Plunger body 407 is cylindrical in shape and is further comprised of latitudinal detent rings 412 and 414, longitudinal anti-torque spline 416, and cleaving ridge 426.

In a preferred embodiment, percutaneous lead anchor 100 and endcap 200 are preloaded into anchor deployment tool 400. The lead anchor is loaded in tube 404 with tines 104 deformed into a straight configuration and held in place by tip 402. Ridges 107 are engaged with slots 420 so that lead channel 106 is aligned with slots 420. Plunger 406 with endcap 200 connected is loaded in the opposing end of tube 404.

Figure 4A:
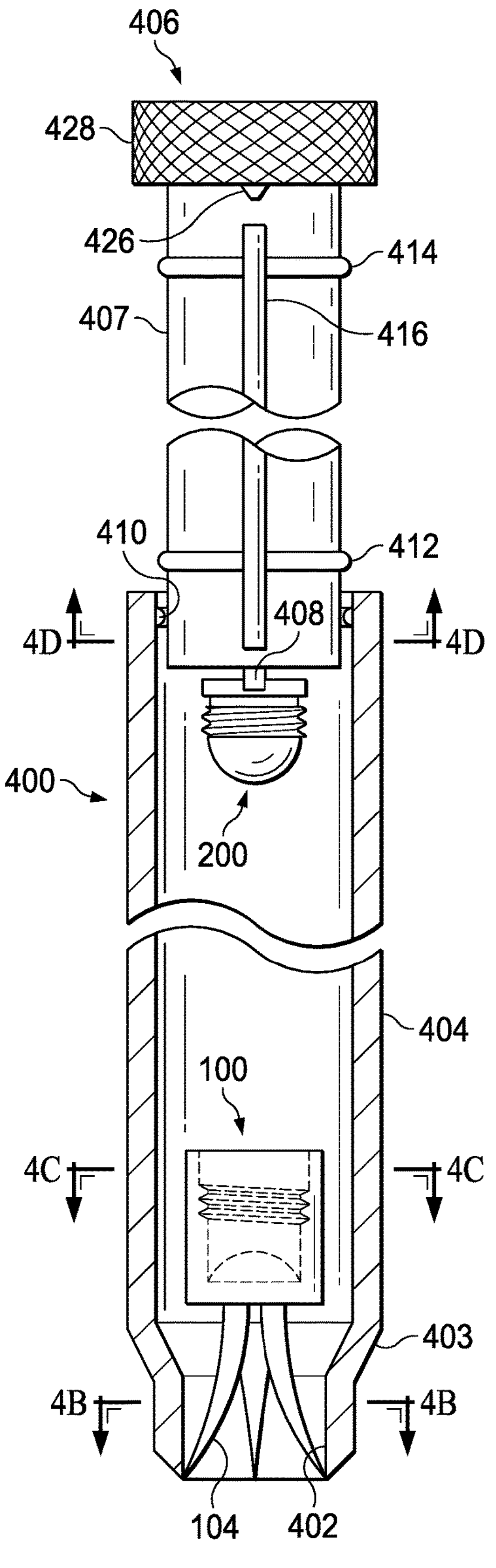
FIG. 4A is a cross-sectional side view of an anchor deployment tool.
Figure 4B:
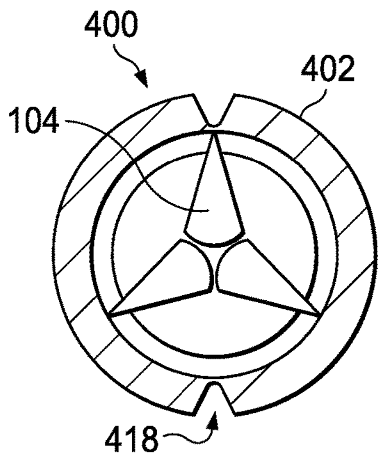
FIG. 4B is a cross-sectional view of an anchor deployment tool.
Figure 4C:
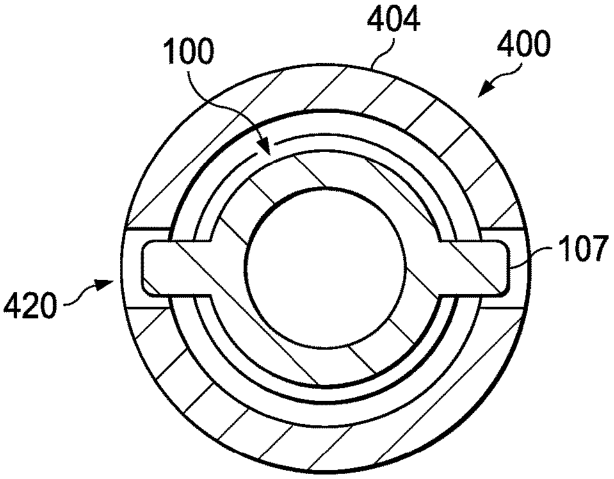
FIG. 4C is a cross-sectional view of an anchor deployment tool.
Figure 4D:
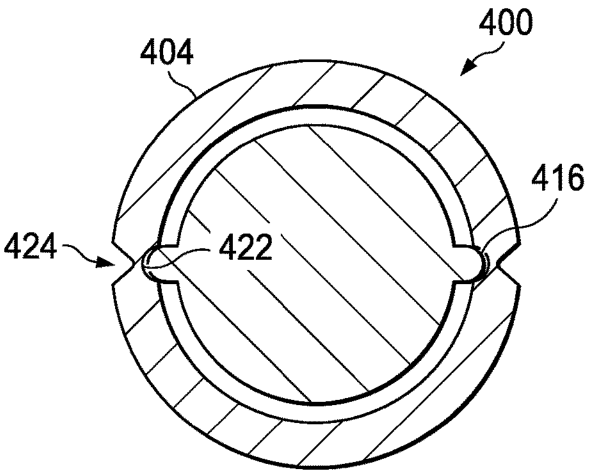
FIG. 4D is a cross-sectional view of an anchor deployment tool.
Figure 4E:
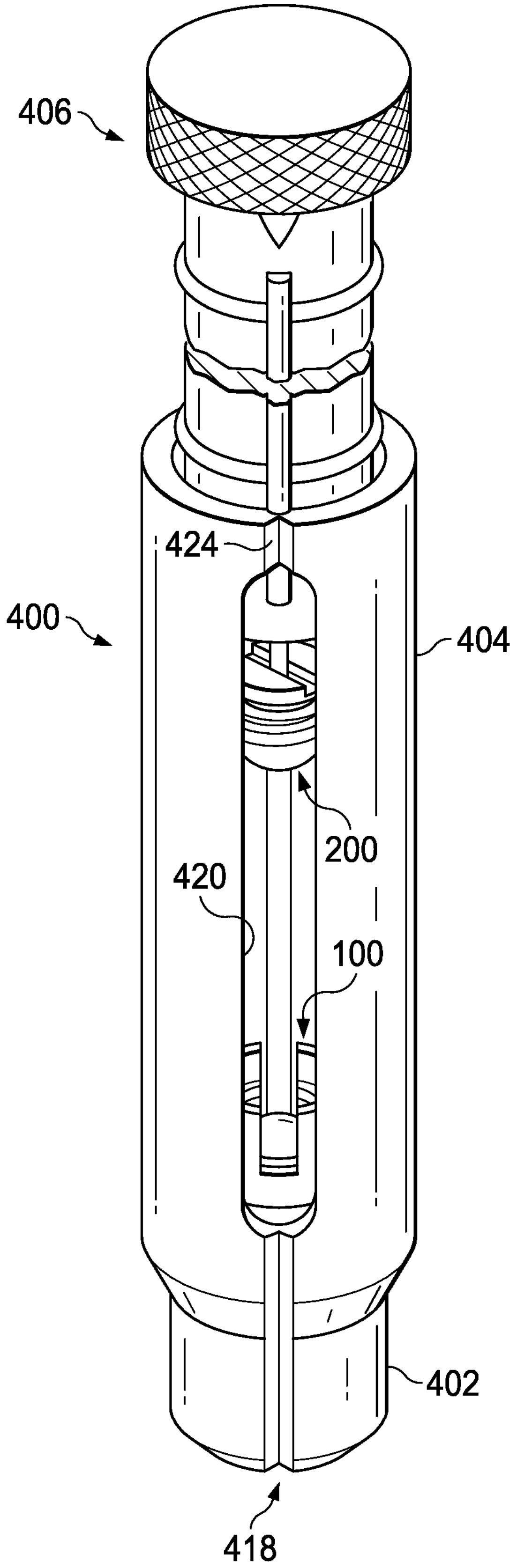
FIG. 4E is an isometric view of an anchor deployment tool.
Figure 4F:
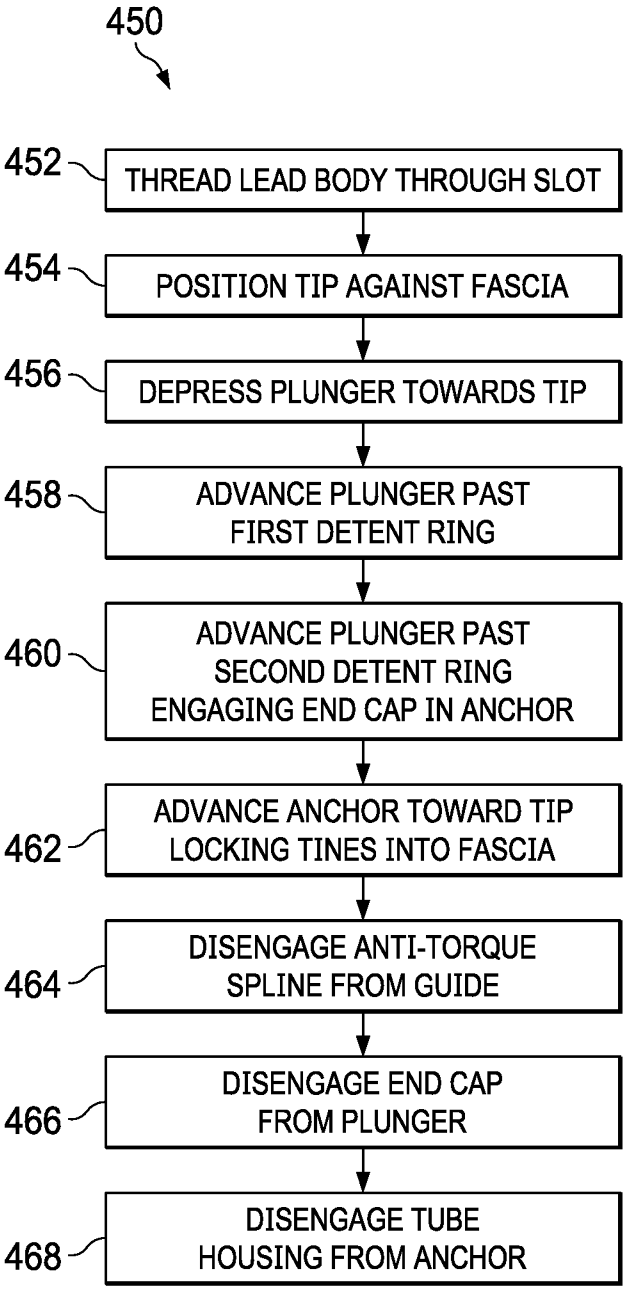
FIG. 4F is a flowchart of a method of use for a preferred embodiment of the anchor deployment tool.

Referring then to FIG. 4F, method of use 450 will be further described. In use, anchor deployment tool 400 functions much as a hypodermic syringe.

At step 452, percutaneous lead body 300 is threaded through slots 420.

At step 454, tip 402 is pressed against the fascia.

At step 456, plunger 406 is depressed. The plunger pushes the endcap 200 downward towards percutaneous lead anchor 100.

At step 458, the plunger is pushed past a first detent ring 412. Detent ring 412 resists insertion of plunger 406 past detent blocking ring 410. This prevents plunger 406 from collapsing slot 420 until pressure is applied to knob 428. Detent ring 414 resists insertion past detent blocking ring 410 just prior to endcap 200 engaging percutaneous lead anchor 100 providing tactile feedback.

At step 460, the plunger is pushed in past detent ring 414, causing endcap 200 to push percutaneous lead body 300 downward into lead channel 106. The lead body is compressed between bevels 108 and 202 and endcap threads 204 deformably engage anchor threads 110.

At step 462, plunger 406 is further depressed, resulting in percutaneous lead anchor 100 being pushed further toward tip 402 and tines engaging the fascia. As the tines engage the fascia, they diverge and lock into the fascia.

At step 464, as tip 402 is continuously pressed against the fascia and plunger 406 is further depressed, anti-torque spline 416 disengages from spline guide 422.

At step 466, knob 428 on the plunger is rotated to break flash 408 to disengage endcap 200 from plunger 406 while counter-rotation force is applied by ridges 107 on the lead anchor which are engaged in slots 420.

At step 468, as the plunger is further depressed, percutaneous lead anchor 100 is driven against the inner surface of tip 402 which causes tube 404 housing to fracture at notches 418 to disengage from the anchor. If anchor deployment tool 400 does not completely disengage by fracture through both notches 418, then cleaving ridge 426 may pressed against cleaving notches 424. The two halves of tube 404 may then be pulled apart, completely disengaging anchor deployment tool 400 from the assembled lead anchor.

Figure 5:
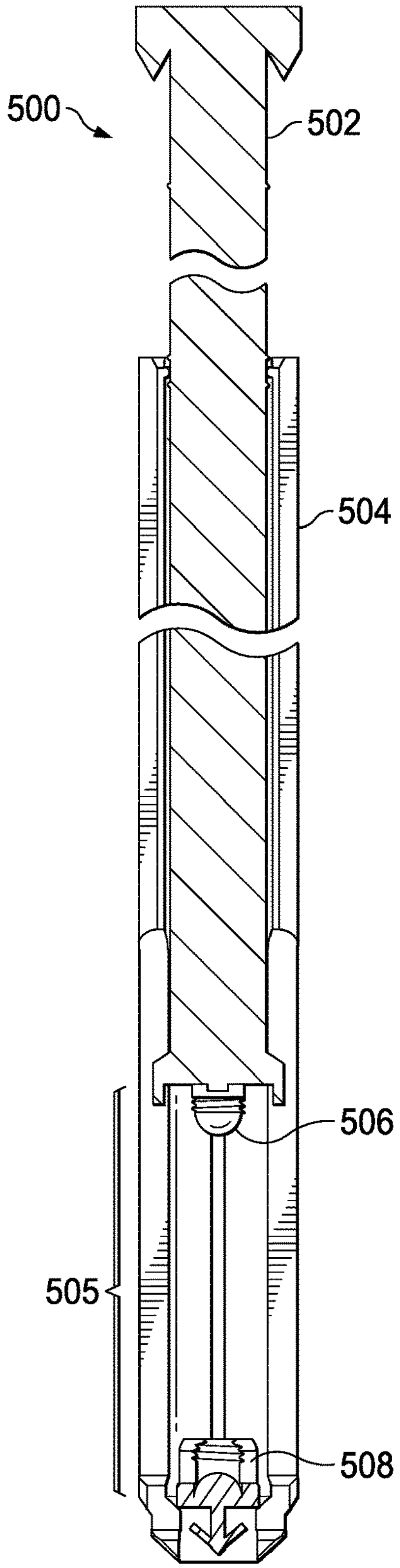
FIG. 5 is a cross-sectional view for a preferred embodiment of a lead anchor and deployment tool.
Figure 6A:
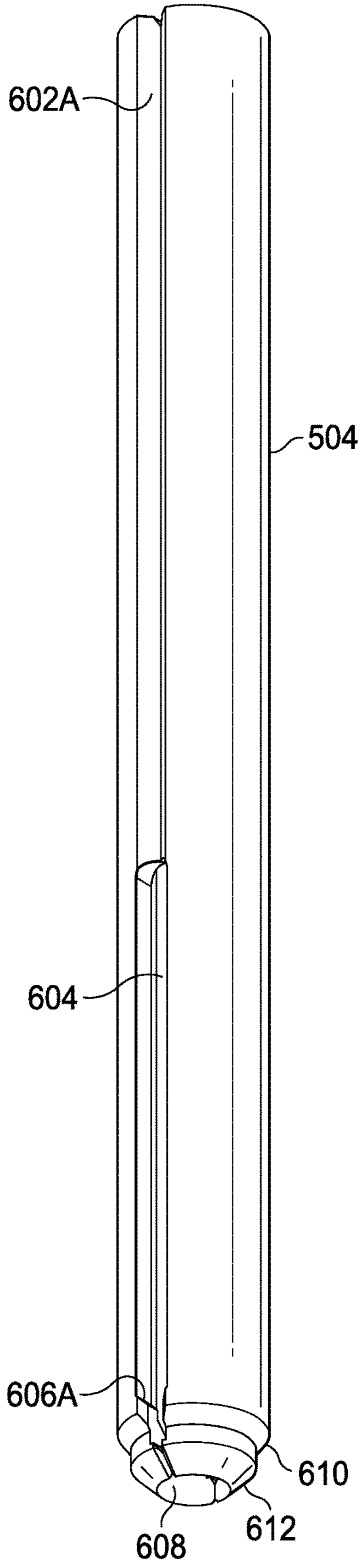
FIG. 6A is an isometric view of a preferred barrel.
Figure 6B:
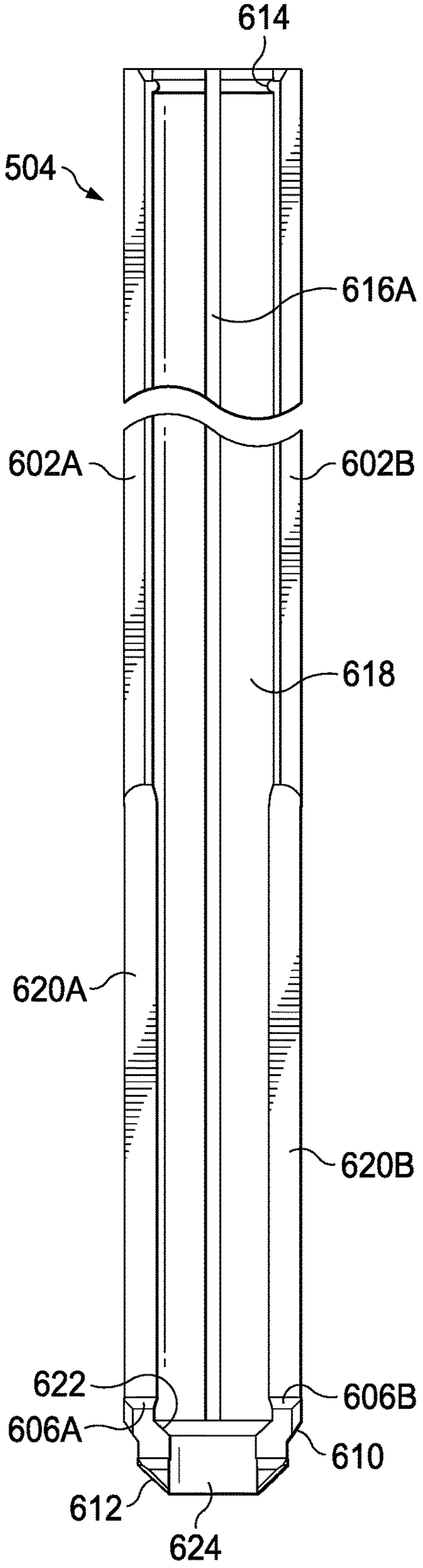
FIG. 6B is a cross-section view of a preferred barrel.
Figure 6C:
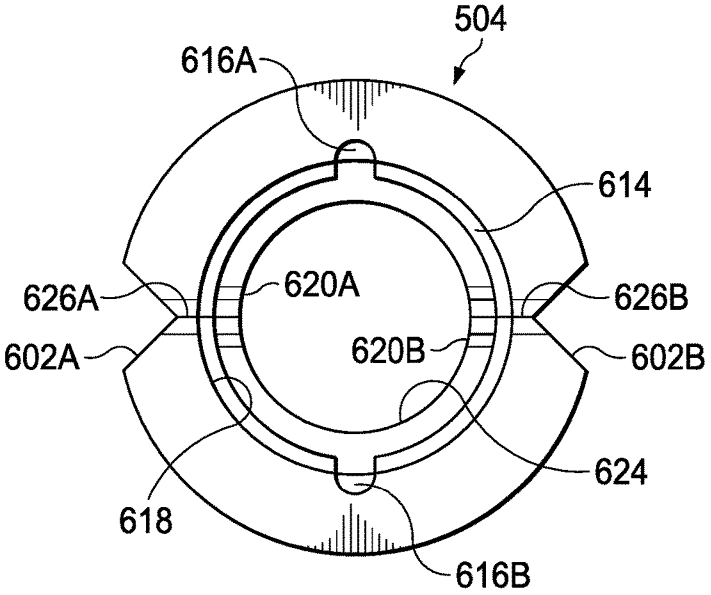
FIG. 6C is a top view of a preferred barrel.
Figure 6D:
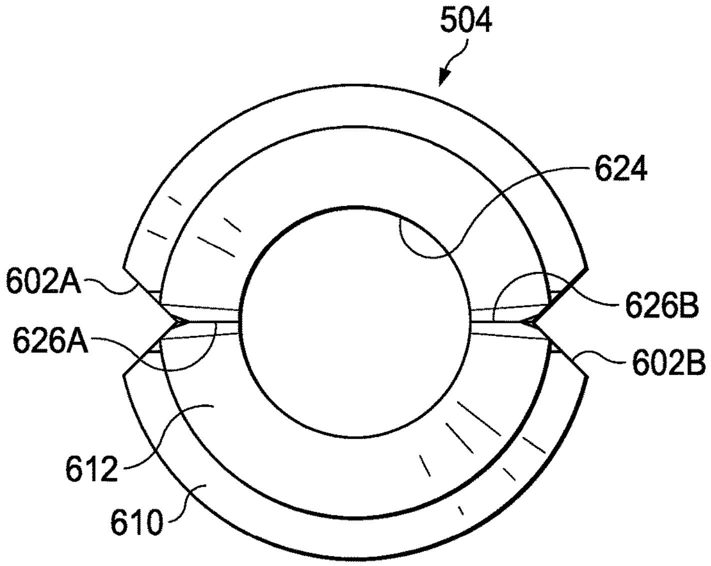
FIG. 6D is a bottom view of a preferred barrel.

Referring, then, to FIG. 5, an alternate embodiment of lead anchor and deployment tool 500 will be further described.

Lead anchor and deployment tool 500 is comprised of plunger 502, barrel 504, and lead anchor assembly 505. Plunger 502 is operationally disposed within barrel 504 and constrained to move coaxially within barrel 504, as will be further described.

Lead anchor assembly 505 is further comprised endcap 506 and anchor body 508. The anchor body is fixed at the distal end of the barrel. The endcap is fixed to the plunger, as will be further described.

Referring to FIGS. 6A, 6B, 6C, and 6D, barrel 504 will be further described.

In general, barrel 504 is a hollow cylindrical tube made of a frangible plastic in design to "break away" from the lead anchor assembly once it is deployed. Barrel 504 includes cylindrical internal plunger guide channel 618. Barrel 504 terminates with anchor guide channel 608 adjacent taper 612 and taper 610. Taper 612 and taper 610, are both frustoconical constrictions which narrow the diameter of barrel 504 and aid in positioning the tool in the fascia, as will be further described.

Barrel 504 is further comprised of lead slot 620A and lead slot 620B. Lead slot 620A and lead slot 620B are diametrically opposed longitudinal openings in barrel 504, which facilitate entry and positioning of the lead body, as will be further described. Lead slot 620A terminates at barrel separation groove 602A and wedge receiver 606A. Lead slot 620B terminates at barrel separation groove 602B and wedge receiver 606B. Barrel separation groove 602A and 602B are generally longitudinal angular slots which traverse the outer surface of the barrel. Wedge receiver 606A and 606B include angular surfaces adapted to interface with wedge 714A and 714B, as will be further described. Wedge receiver 606A terminates at break line 626A. Wedge receiver 606B terminates at break line 626B. The break lines are generally thin plastic flashing designed to rupture upon application of sufficient pressure to the wedge receivers.

Barrel 504 is further comprised of internal spline receiver 616A and internal spline receiver 616B. The internal spline receivers are diametrically opposed longitudinal slots which run the length of anchor guide channel 624. In a preferred embodiment, the internal spline receivers are spaced about 90° from the lead slots with respect to the central longitudinal axis of barrel 504.

Barrel 504 is further comprised of detent blocking of ring 614. In general, detent blocking ring 614 is a fixed annular ring, having a generally semi-circular cross-section positioned at the proximal end of barrel 504 and adapted to contact detent rings on the plunger, as will be further described.

Figure 7A:
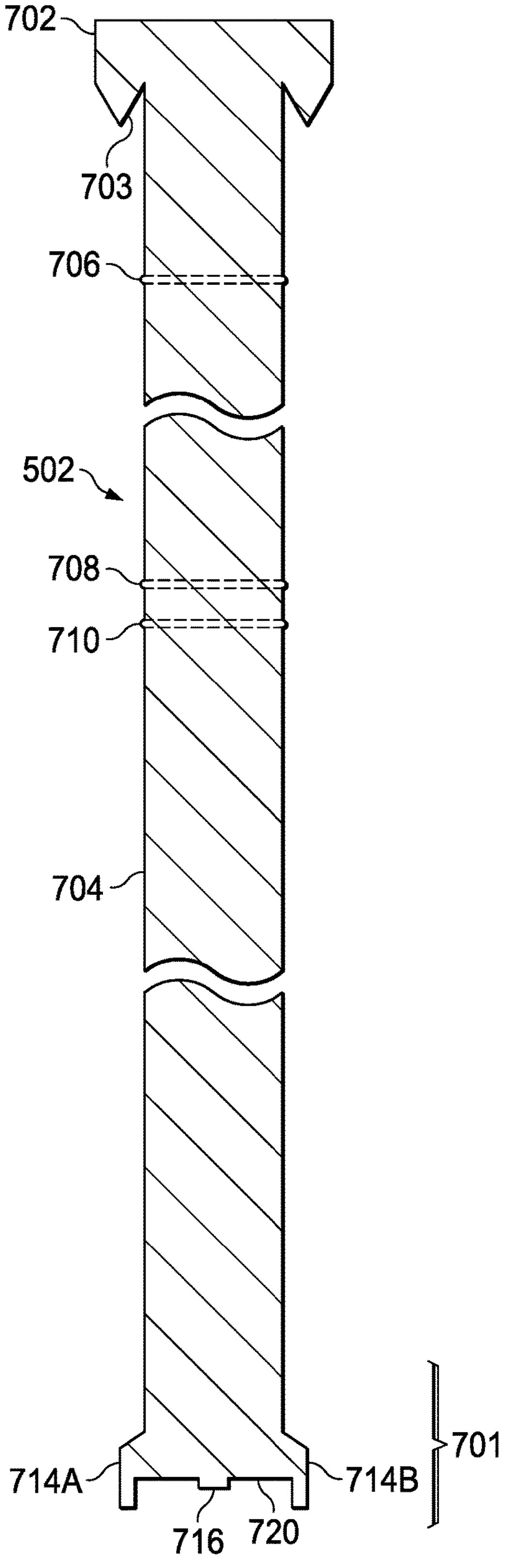
FIG. 7A is a cross-section view of a preferred plunger.
Figure 7B:
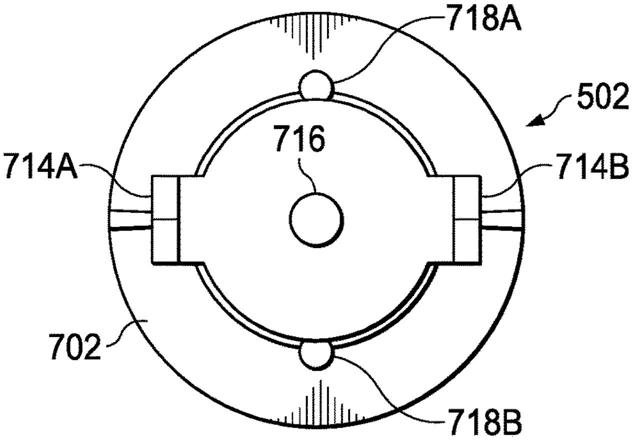
FIG. 7B is a bottom view of a preferred plunger.
Figure 7C:
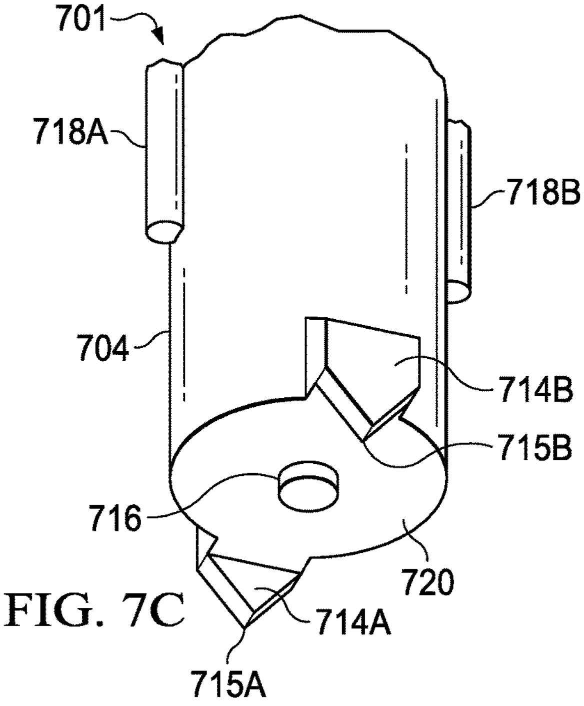
FIG. 7C is a detailed view of a preferred plunger.

Referring then to FIGS. 7A, 7B, and 7C, plunger 502 will be further described.

Plunger 502 is generally a solid cylinder further comprising plunger top 702, plunger shaft 704 and connector head 701. In a preferred embodiment, plunger 502 is constructed from a rigid plastic, such as polypropylene, polystyrene or Delrin.

Plunger top 702 is generally flat and cylindrical and integrally formed with plunger shaft 704. The underside of plunger top 702 includes annular retainer groove 703. Retainer groove 703 is adapted to retain the broken pieces of barrel 504 after use, as will be further described.

Plunger shaft 704 includes detent ring 706, detent ring 708, and detent ring 710. In general, each of the detent rings is fixed on the exterior of plunger shaft 704, and is annular and has a generally semicircular cross-section.

Plunger shaft 704 further comprises integrally formed spline 718A and spline 718B. In general, each of the splines has a semi-circular cross-section, and traverses the length of the plunger shaft from plunger top 702 to connector head 701. In a preferred embodiment, spline 718A is diametrically opposed from spline 718B. Spline 718A and spline 718B are adapted to engage spline receiver 616A and spline receiver 616B, respectively, as will be further described. The splines prevent the rotation of the plunger in the barrel about the central axis of the tool and assure proper alignment of the end cap with the anchor body.

Connector head 701 is further comprised of wedges 714A and 714B. In general, wedges 714A and 714B are triangular members, which extend radially from plunger shaft 704 and which are diametrically opposed across the central axis of the plunger. Each of the wedges is positioned approximately 90° from each of the splines, about the central axis of the plunger shaft. Wedge 714A includes fracture tip 715A. Wedge 714B includes fracture tip 715B. Each of the fracture tips extends below engagement surface 720 and is adapted to engage wedge receiver 606A and wedge receiver 606B, as will be further described.

Connector head 701 further comprises engagement surface 720 at the base of plunger shaft 704. Engagement surface 720 is generally flat and circular and adapted to abut the engagement surfaces of the anchor body, as will be further described. Engagement surface 720 supports integrally formed connector 716. In general, connector 716 is cylindrical and of smaller diameter than plunger shaft 704. Connector 716 is adapted to engage a slot of the end cap and hold it in position against the engagement surface, as will be further described.

Figure 8:
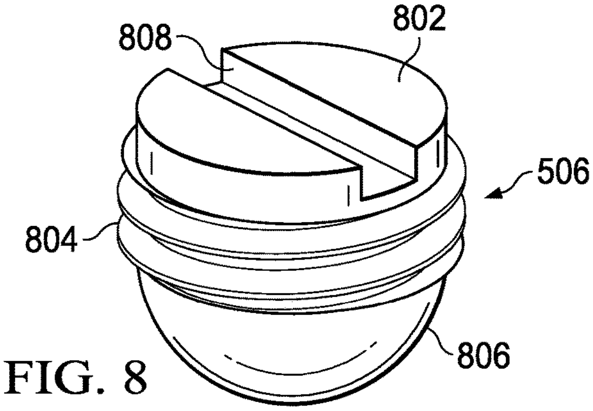
FIG. 8 is an isometric view of a top for a preferred lead anchor assembly.
Figure 9B:
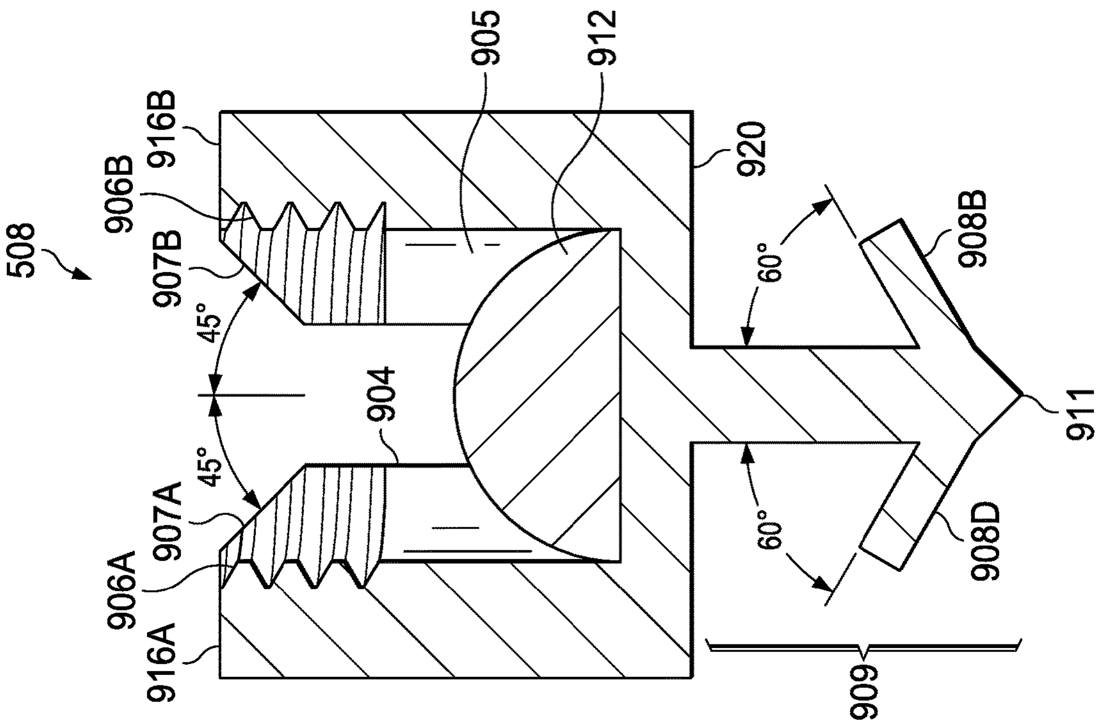
FIG. 9B is a cross-section view of a preferred anchor body.
Figure 9A:
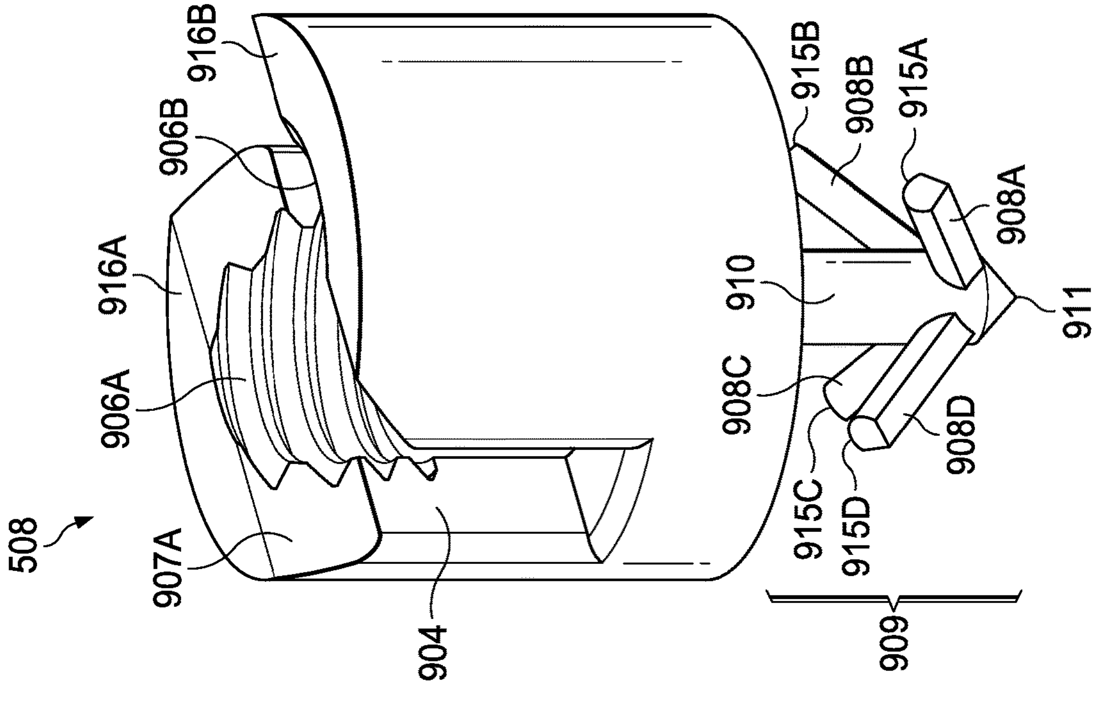
FIG. 9A is an isometric view of a preferred anchor body.
Figure 9C:
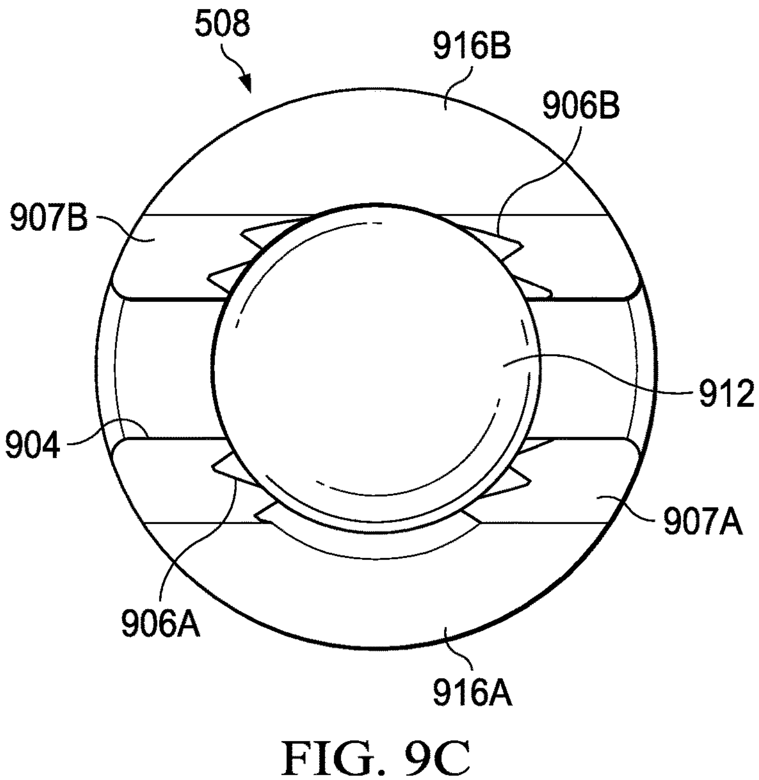
FIG. 9C is a top view of a preferred anchor body.
Figure 9D:
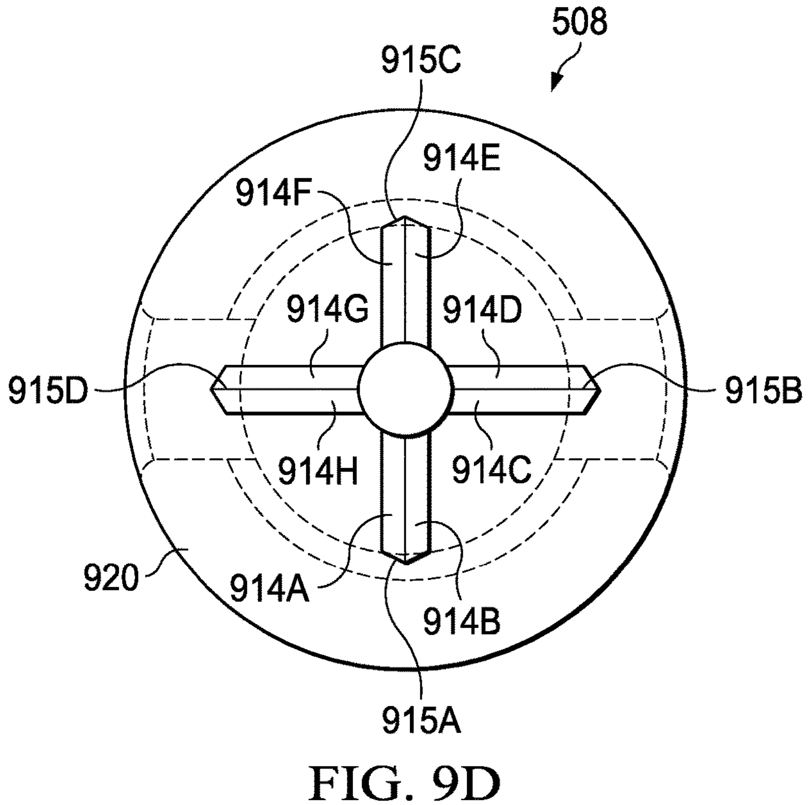
FIG. 9D is a bottom view of a preferred anchor body.
Figure 10B:
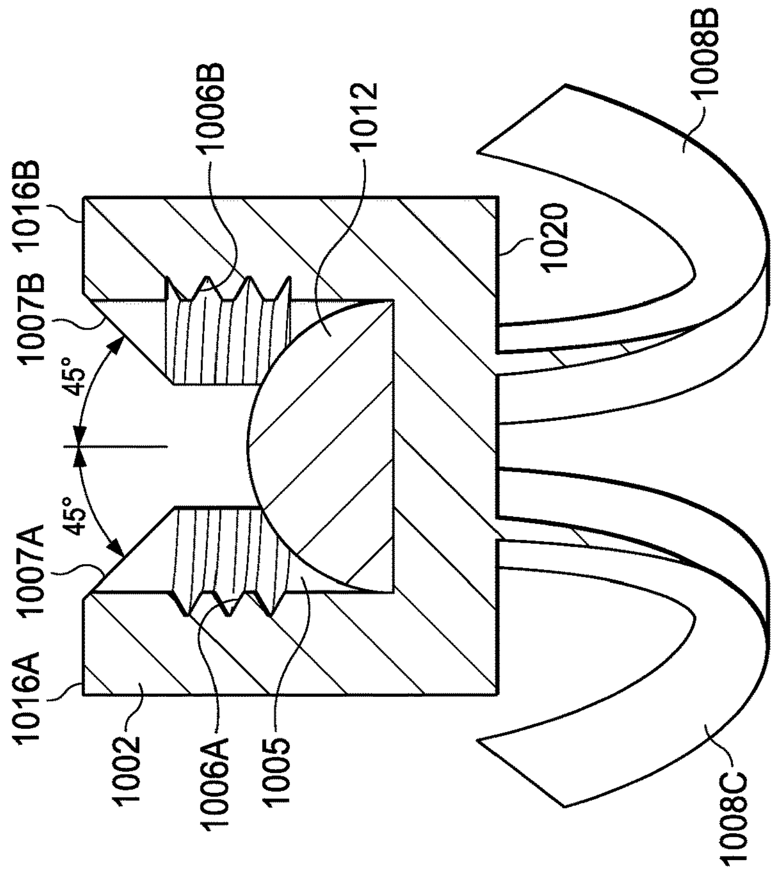
FIG. 10B is a cross-section view of a preferred anchor body.
Figure 10A:
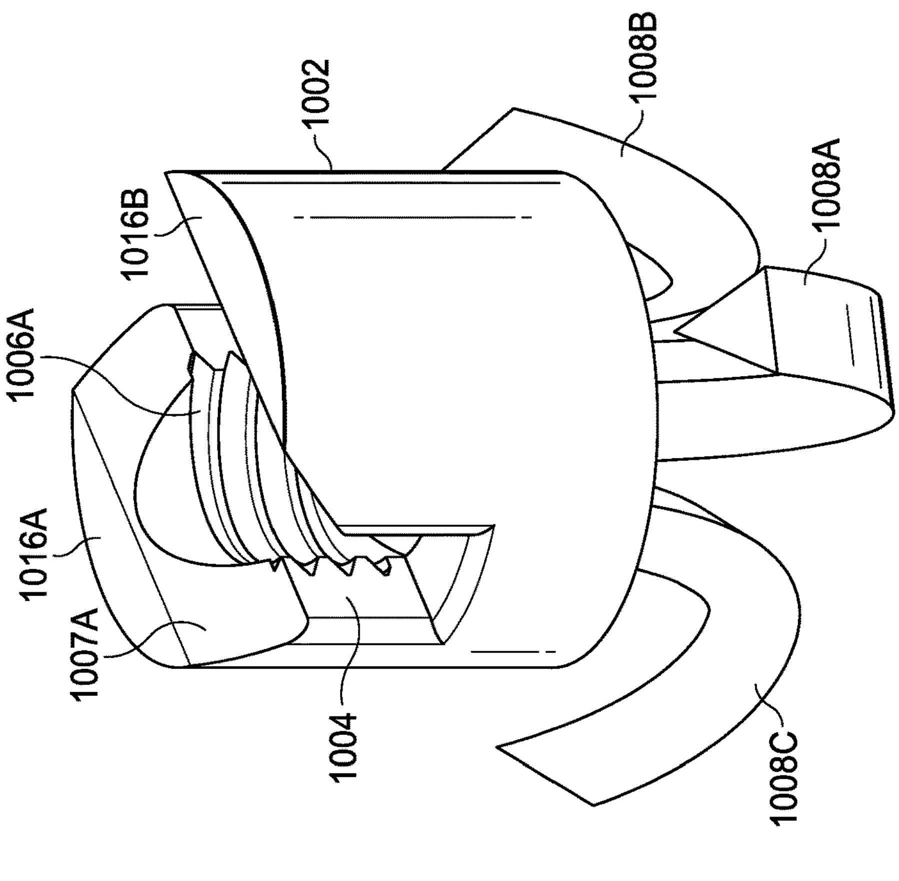
FIG. 10A is an isometric view of a preferred anchor body.
Figure 10C:
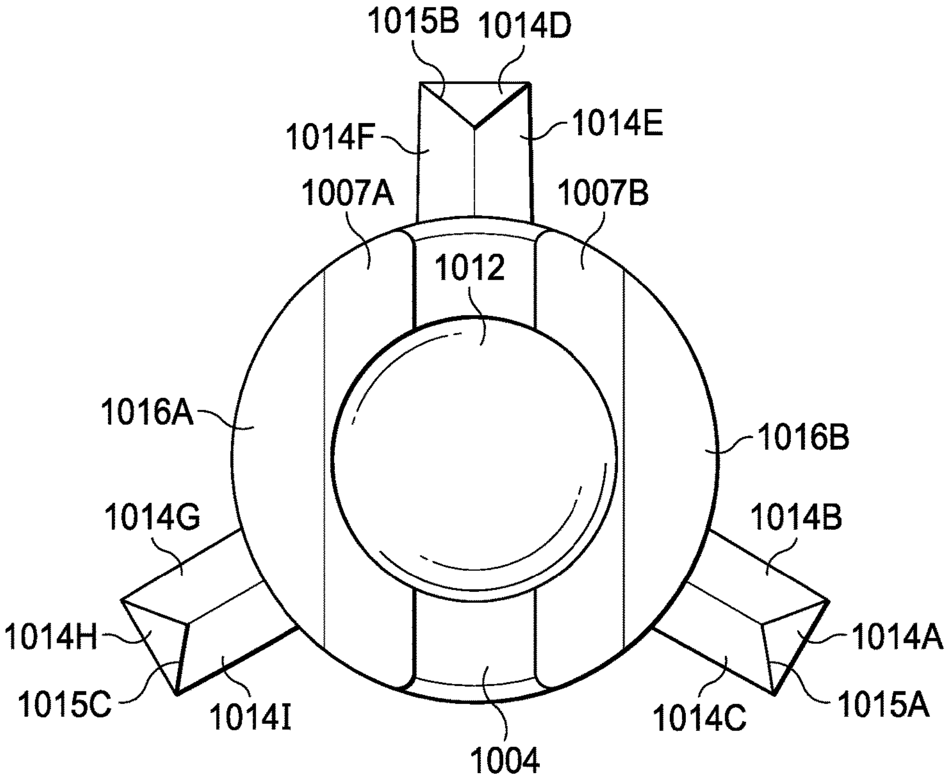
FIG. 10C is a bottom view of a preferred anchor body.
Figure 10D:
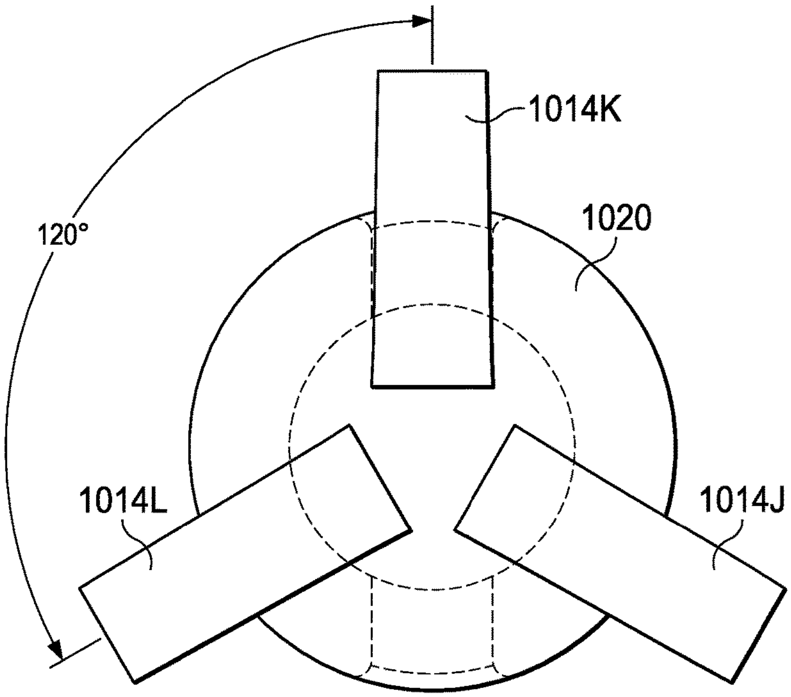
FIG. 10D is a bottom view of a preferred anchor body.

Referring then to FIG. 8, endcap 506 will be further described.

Endcap 506 is comprised of nylon 12, or similarly malleable material, such as polyether ether ketone. Endcap 506 is generally cylindrical and is comprised of top 802, threads 804, and flex dome 806.

Top 802 further comprises slot 808, which is adapted to accept a bladed screwdriver. Slot 808 might also take the form of a spanner or Phillips head adaptation. In other embodiments, slot 808 can include an octagonal head adapted to accept a socket and ratchet combination.

Threads 804 are positioned on the exterior surface of the endcap and are adapted to engage half threads in the anchor body, as will be further described.

Flex dome 806 is generally semi-spherical in shape and is integrally formed on the anchor body adjacent threads 804. In a preferred embodiment, the flexibility of threads 804 allows anchor body 508 to be engaged with the half threads of the anchor body by a press fit. As a result of the press fit, threads 804 are deformed. However, upon rotation of top 802, the threads are designed to engage the half threads of the anchor body and which allows the endcap to be removed by rotation.

Referring to FIGS. 9A, 9B, 9C and 9D, anchor body 508 will be further described.

Anchor body 508 is generally cylindrical and is composed of titanium, stainless steel, nylon 12, Teflon or Delrin. Other rigid, medical grade plastics or inert metallic alloys will also suffice.

Anchor body 508 includes lead slot 904. Lead slot 904 is generally rectangular in cross-section and diametrically spans anchor body 508. Cylindrical access bay 905 surrounds lead slot 904, and is coaxial with the longitudinal axis of the anchor body. Half threads 906A and 906B are formed in axis bay adjacent lead slot 904. In a preferred embodiment, half threads 906A and 906B are diametrically opposed and positioned at the proximal end of access bay 905.

Half threads 906A are directly adjacent to angular centering surface 907A and engagement surface 916A. Likewise, half threads 906B are directly adjacent centering surface 907B and engagement surface 916B. Engagement surfaces 916A and 916B are adapted to contact engagement surface 720 of plunger shaft 704 during use of the tool, as will be further described. Centering surfaces 907A and 907B are sloped at about 45° with respect to the central axis of the anchor body and are adapted to direct the lead body into lead slot 904, as will be further described.

Access bay 905 further comprises flex dome 912. Flex dome 912 is preferably integrally formed with anchor body 508. However, in other embodiments, flex dome 912 can be formed of a flexible material such as a butyl rubber which is fixed in the anchor bay by a suitable adhesive.

Anchor body 508 further comprises downwardly disposed grappling hook 909. Grappling hook 909 includes hook shaft 910 and angular claws 908A, 908B, 908C and 908D. Hook shaft 910 preferably is coaxial with anchor body 508 and extends downward from bottom surface 920. Hook shaft 910 terminates distally at conical tip 911. Hook shaft 910 is preferably integrally formed with angular claws 908A, 908B, 908C, and 908D. In a preferred embodiment, claw 908A is diametrically opposed to claw 908B, likewise, preferably, claw 908B is diametrically opposed from a claw 908D. Preferably, each of the claws extends upwardly from tip 911 toward bottom surface 920 at an angle of approximately 60°.

Each of the claws includes a complex cross section comprised of two opposing angular claw surfaces and a semicircular dome. Claw 908A further comprises claw surface 914A and 914B. Claw surface 914A and 914B are joined by sharpened edge at 915A. Claw 908B further comprises claw surface 914C and claw surface 914D. Claw surface 914C and claw surface 914D meet at sharpened edge 915B. Claw 908C further comprises claw surface 914E and claw surface 914F. Claw surfaces 914E and 914F are joined by sharpened edge 915C. Likewise, claw 908C further comprises claw surface 914G and 91411. Claw surface 914G and claw surface 91411 are joined by sharpened edge 915D.

Referring to FIGS. 10A, 10B, 10C and 10D, an alternate embodiment of the anchor body will be further described.

Anchor body 1002 is generally cylindrical and composed of titanium, stainless steel, nylon 12, Teflon or Delrin. Anchor body 1002 includes generally rectangular lead slot 1004 which, preferably, is positioned latitudinally across the diameter of the anchor body. Lead slot 1004 is bounded by centering surface 1007A and centering surface 1007B. Centering surface 1007A is bounded by engagement surface 1016A. Centering surface 1007B is bounded by engagement surface 1016B. Engagement surface 1016A and 1016B are preferably perpendicular to the longitudinal axis of the anchor body. Each of the engagement services makes an angle of approximately 45° with the central axis of the anchor body.

Lead slot 1004 traverses generally cylindrical access bay 1005. Access bay 1005 generally forms a cylindrical cavity coaxial with the central axis of the anchor body. Anchor body 1002 is terminated in flex dome 1012. Flex dome 1012 is generally hemispherical and upwardly oriented at the base of access bay, coaxial with the longitudinal axis of the anchor body. Flex dome 1012 and in one embodiment is integrally formed with the anchor body. In another embodiment flex dome 1012 is comprised of a flexible butyl rubber fixed at the base of the anchor bay by a suitable medical adhesive.

Half threads 1006A are positioned in access bay 1005, adjacent centering surface 1007A. Likewise, half threads 1006B are positioned in access bay 1005, adjacent centering surface 1007B. Each functions as previously described.

Anchor body 1002 further comprises bottom surface 1020. Arcuate claw 1008A, arcuate claw 1008B, and arcuate claw 1008C extend downwardly from bottom surface 1020. Each arcuate claw generally forms a semicircular flexible hook.

Each arcuate claw generally has a triangular cross-section with an upwardly facing sharpened edge. Arcuate claw 1008A further comprises upwardly facing claw surfaces 1014A, 1014B, and 1014C. Claw surfaces 1014A, 1014B, and 1014C are joined by sharpened edge 1015A. Likewise, arcuate claw 1008B further comprises upwardly facing claw surfaces 1014D, 1014E and 1014F. Upwardly facing claw surfaces 1014D, 1014E, and 1014F are joined by sharpened edge 1015B. Similarly, arcuate claw 1008C is further comprised of upwardly facing claw surfaces 1014G, 1014H, and 1014I. Upwardly facing claw surfaces 1014G, 1014H, and 1014I are joined by sharpened edge 1015C.

Each arcuate claw further comprises a downwardly facing flat claw surface. Arcuate claw 1008A includes downwardly facing claw surface 1014J. Likewise, arcuate claw 1008B includes downwardly facing claw surface 1014K. Arcuate claw 1008C includes downwardly facing claw surface 1014L. Each of the arcuate claws is disposed at a 120° angle with respect to the other arcuate claws, with respect to the central longitudinal axis of the anchor body. In other embodiments, other numbers of arcuate claws may be included.

Figure 11:
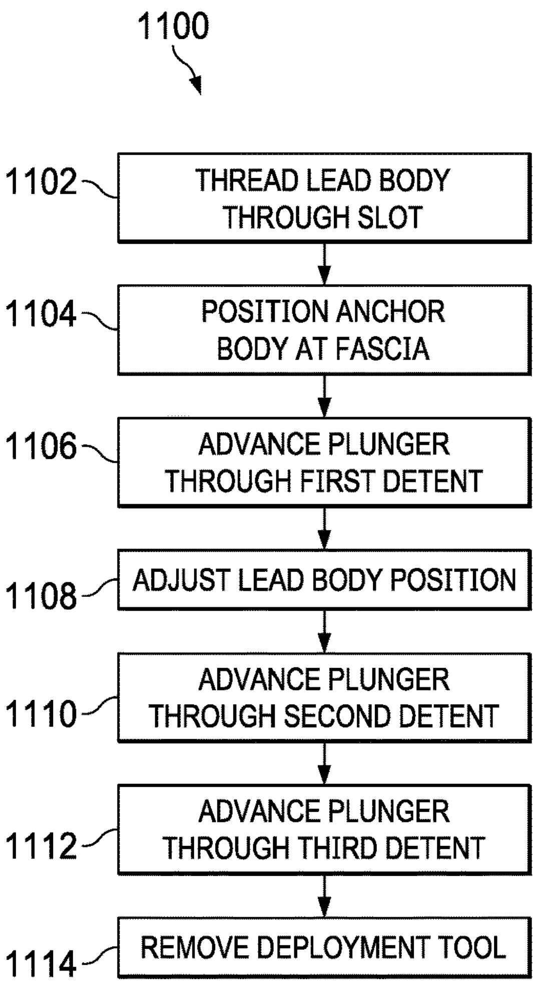
FIG. 11 is a flowchart of a method of use of a preferred lead anchor and deployment tool.

Referring then to FIG. 11, method 1100 of deploying the lead anchor assembly will be further described.

When assembled, plunger 502 resides coaxially within barrel 504. Splines 718A and 718B move within, and are constrained by, spline receivers 616A and 616B, respectively. Endcap 506 is fixed adjacent engagement surface 720 and held in place by a friction fit between connector 716 and slot 808. Wedges 714A and 714B are constrained to move longitudinally within lead slot 604.

Anchor body 508 is positioned adjacent and fixed to anchor centering surface 622 with a suitable medical grade adhesive. Grappling hook 909 is resident within anchor guide channel 624, adjacent taper 610 and taper 612.

Alternatively, anchor body 1002 may be removably fixed to anchor centering surface 622 with a suitable, releasable medical grade adhesive. In this case, the arcuate claws are resident within the anchor guide channel.

At step 1102, a lead body is threaded through lead slot 620A and lead slot 620B of the barrel and the lead slot of the anchor body. Preferably, the engagement surfaces are used to position the anchor lead securely within the lead slot and against the flex dome of the anchor body.

At step 1104, taper 612 and taper 610 are used to position barrel 504 in appropriate location in the deep fascia.

At step 1106, plunger 502 is advanced such that detent ring 710 deforms and passes detent blocking ring 614. As it does, endcap 506 is advanced into the anchor body such that threads 804 come in contact with the half threads of the anchor body, thereby trapping the lead body in the access bay and the lead slot between flex dome 806 and the flex dome of the anchor body. However, at this step, neither of the flex domes is deformed and the lead body may still be moved axially within the lead slot.

At step 1108, the lead body position is adjusted axially, if required.

At step 1110, plunger 502 is advanced within barrel 504 such that detent ring 708 deforms and passes detent blocking ring 614. In this position, flex dome 806 compresses the lead body against the flex dome of the anchor body, thereby securing it in place. Threads 804 deform when entering the half-threads of the anchor body and secure the lead body in place.

At step 1112, plunger 502 is further advanced within barrel 504 such that detent ring 706 deforms and passes detent blocking ring 614. In this position, wedges 714A and 714B encounter and expand wedge receivers 606A and 606B, respectively. As the wedges advance in the wedge receivers, break line 626A and break line 626B fracture thereby releasing anchor body 508 from anchor centering surface 622. Further advancing plunger 502 forces the lead anchor assembly into the fascia thereby securing either grappling hook 909 or the arcuate claws in the fascia. Simultaneously, barrel 504 fractures along barrel separation groove 602A and barrel separation groove 602B. At the same time, the fractured barrel is frictionally secured within retainer groove 703 of plunger top 702.

At step 1114, the deployment tool, including the plunger and the fractured barrel, are removed and discarded, leaving the lead anchor assembly secured in the fascia.

Figure 12:
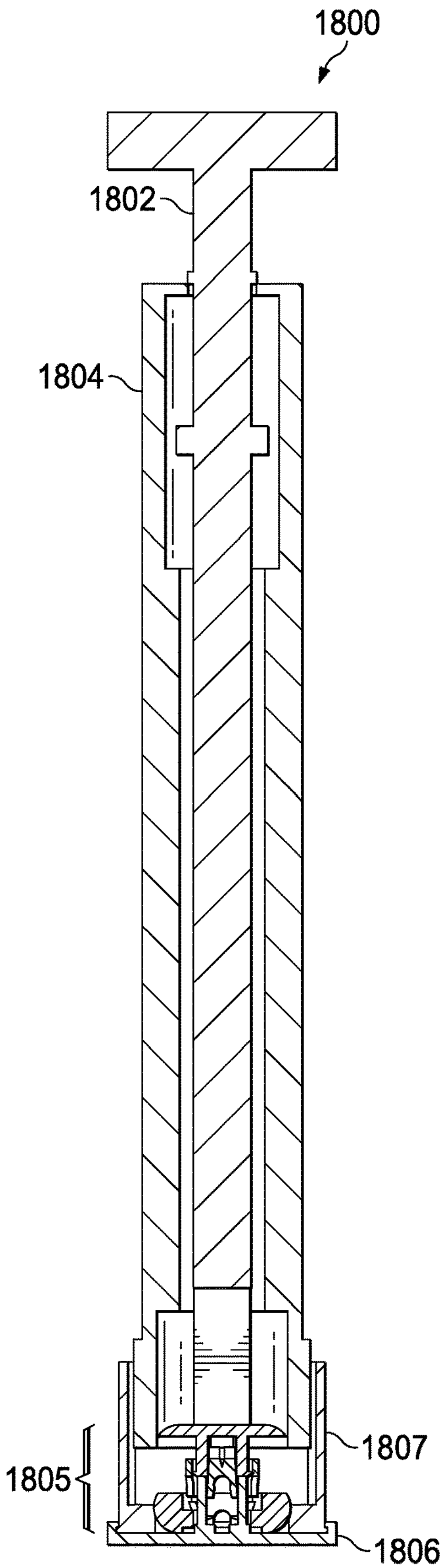
FIG. 12 is a cross-section view of an alternate embodiment of a lead anchor and deployment tool.

Referring to FIG. 12, an alternative embodiment of lead anchor and deployment tool 1800 will be further described.

Lead anchor and deployment tool 1800 comprises barrel 1804, plunger 1802, sliding cartridge 1807, lead anchor assembly 1805 and assembly tower 1806.

Barrel 1804 is generally cylindrical and serves to contain and guide plunger 1802 and lead anchor assembly 1805. Lead anchor and deployment tool 1800 further comprises sliding cartridge 1807. Sliding cartridge 1807 generally contains and positions the lead anchor assembly and functions to aid in deployment of the lead anchor assembly, as will be further described. Sliding cartridge 1807 is constrained to move axially along the exterior of barrel 1804. Lead anchor and deployment tool 1800 further comprises assembly tower 1806. The assembly tower generally prevents movement of lead anchor assembly 1805 until the deployment tool is ready for use, as will be further described. In a preferred embodiment, plunger 1802, barrel 1804, sliding cartridge 1807, lead anchor assembly 1805 and assembly tower 1806 are all coaxial along the central longitudinal axis of the lead anchor and deployment tool.

Figure 13:
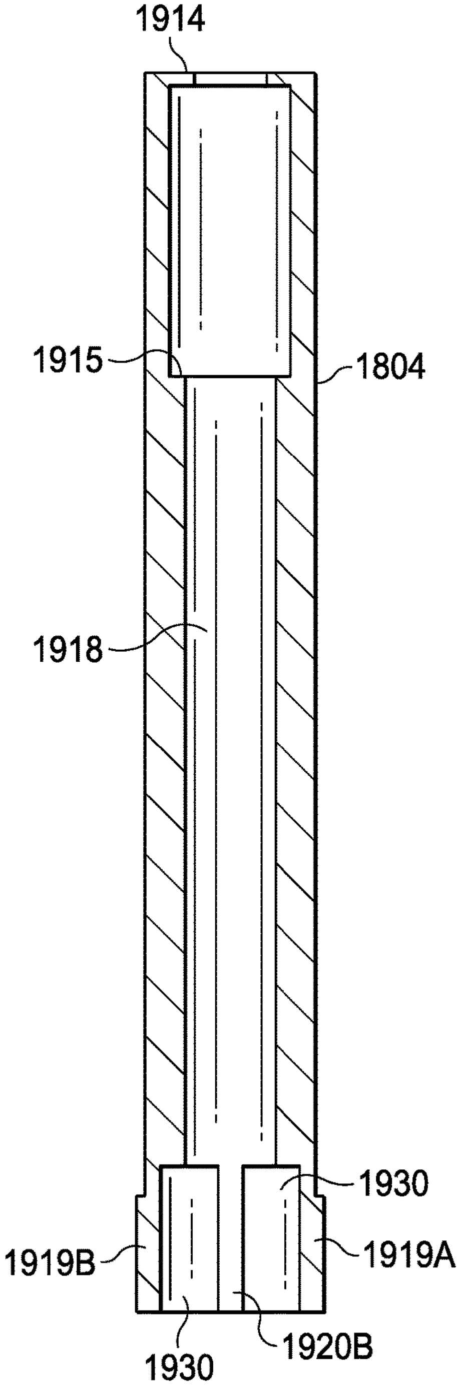
FIG. 13 is a cross section of a preferred barrel.
Figure 14:
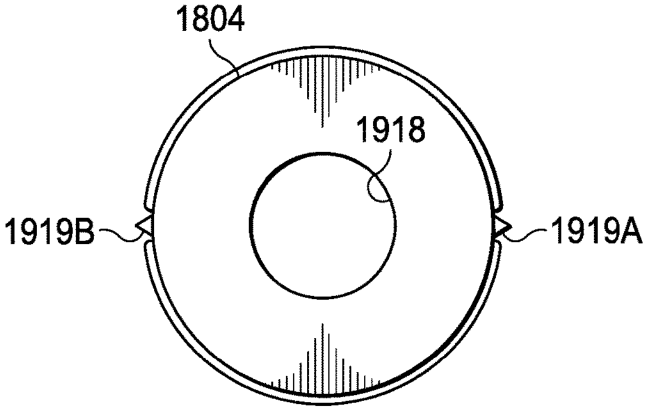
FIG. 14 is a top view of a preferred barrel.
Figure 15:
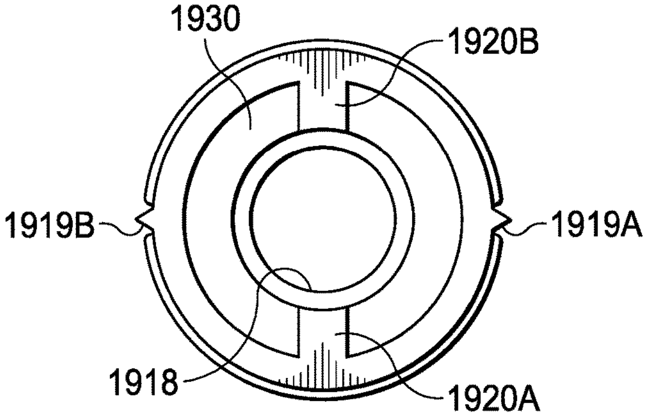
FIG. 15 is a bottom view of a preferred barrel.

Referring to FIGS. 13, 14 and 15, barrel 1804 will be further described. Barrel 1804 is a generally hollow cylinder surrounding plunger guide channel 1918 and deployment bay 1930. In a preferred embodiment, the barrel is manufactured from a medical grade polypropylene or other rigid medical grade plastic. Barrel 1804 further comprises interior annular blocking ring 1914 at its proximal end. Also located at the proximal end of barrel 1804 is plunger stop 1915. Plunger stop 1915 comprises an annular cylindrical interior surface adjacent plunger guide channel 1918 and serves to stop the downward travel of the plunger when the deployment tool is in use, as will be further described.

Barrel 1804 further comprises plunger guide channel 1918, which constrains the movement of plunger 1802 to an axial path. Barrel 1804 further comprises exterior cartridge guides 1919A and 1919B at its distal end. Cartridge guides 1919A and 1919B are ridges of triangular cross-section that are generally parallel to the longitudinal axis of the deployment tool and serve to constrain the motion of sliding cartridge 1807 axially, as will be further described. Barrel 1804 further comprises integrally formed compressor deployment arms 1920A and 1920B. Compressor deployment arms 1920A and 1920B each are generally radial flanges that extend into bay 1930 and serve to engage the lead compressor, as will be further described.

Figure 16:
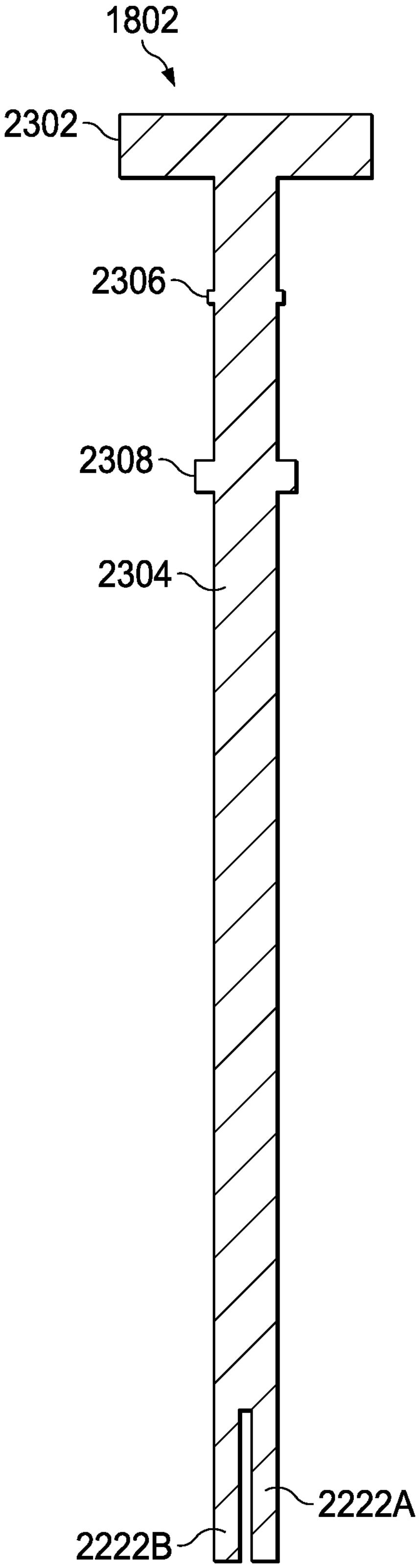
FIG. 16 is a cross-section view of a preferred plunger.
Figure 17:
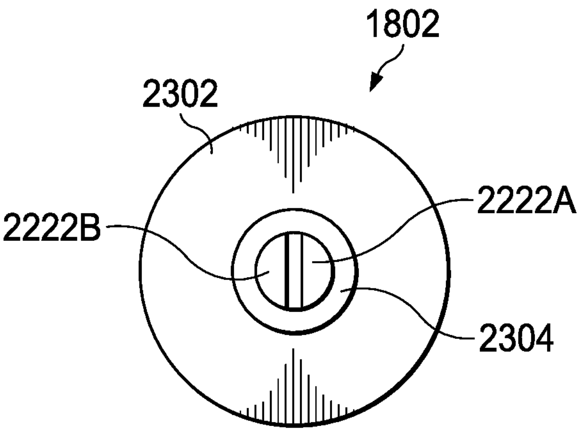
FIG. 17 is a bottom view of a preferred plunger.

Referring to FIGS. 16 and 17, plunger 1802 will be further described.

Plunger 1802 is a generally cylindrical and includes plunger shaft 2304. Plunger shaft 2304 has a circular cross-section and includes plunger top 2302 at its proximal end. The plunger top is generally flat and cylindrical. Plunger shaft 2304 further includes detent rings 2306 and 2308. Detent rings 2306 and 2308 are annular and are formed integrally with plunger shaft 2304. Plunger shaft 2304 further supports cap deployment arms 2222A and 2222B, at its distal end. Cap deployment arm 2222A and cap deployment arm 2222B engage and deploy the anchor cap, as will be further described.

Figure 18:
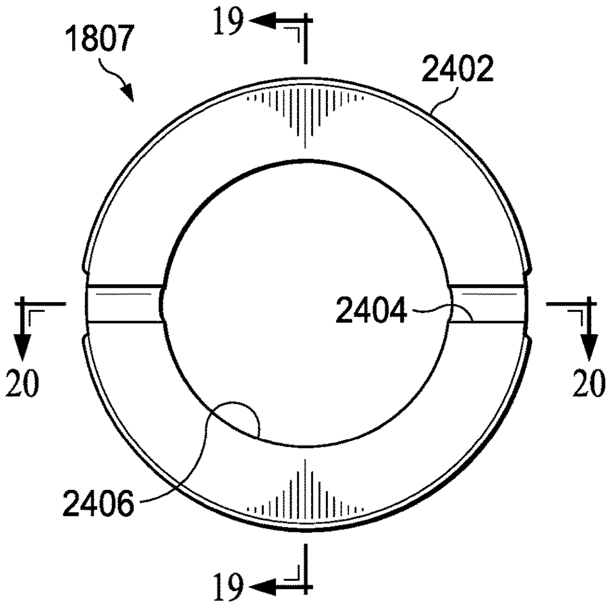
FIG. 18 is a bottom view of a preferred sliding cartridge.
Figure 20:
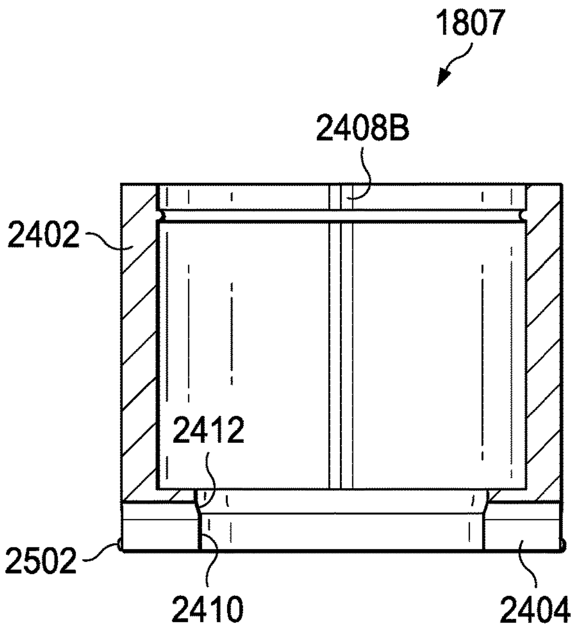
FIG. 20 is a side view of a preferred sliding cartridge.
Figure 19:
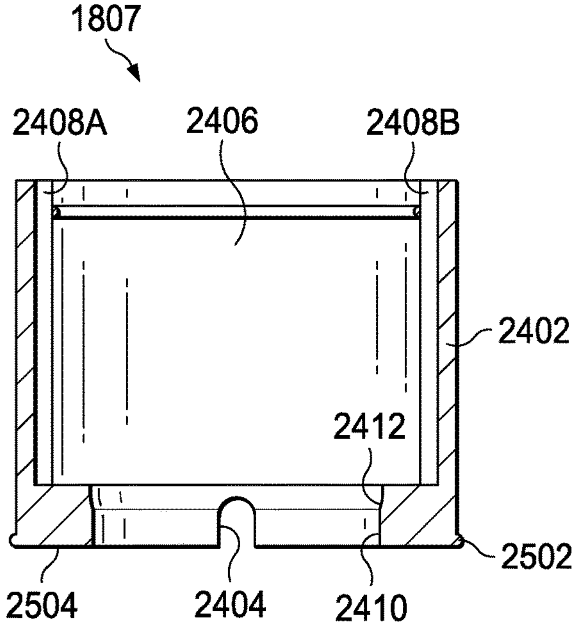
FIG. 19 is a cross-sectional view of a preferred sliding cartridge.

Referring to FIGS. 18, 19 and 20, sliding cartridge 1807 will be further described. Sliding cartridge 1807 is further comprised of cartridge body 2402 is generally hollow and cylindrical. Sliding cartridge body 2402 includes barrel guide chamber 2406. Sliding cartridge body 2402 further comprises interior cartridge guide receivers 2408A and 2408B. Cartridge guide receiver 2408A and cartridge guide receiver 2408B generally form longitudinal channels which engage cartridge guide 1919A and cartridge guide 1919B and constrain sliding cartridge 1807 to longitudinal motion coaxial with the lead anchor and deployment tool.

Sliding cartridge body 2402 further comprises lead channel 2404. Lead channel 2404 traverses the diameter of sliding cartridge body 2402 and serves to accommodate a percutaneous lead body, as will be further described. Sliding cartridge body 2402 further comprises cylindrical base 2504 at its distal end. Base 2504 is generally flat and includes axially oriented anchor exit channel 2410. Anchor exit channel 2410 forms a cylindrical hole in base 2504. Anchor exit channel 2410 includes toroid support ring 2412. Toroid support ring 2412 is adapted to engage an exterior surface of the toroid of the lead anchor assembly, as will be further described.

Figure 21:
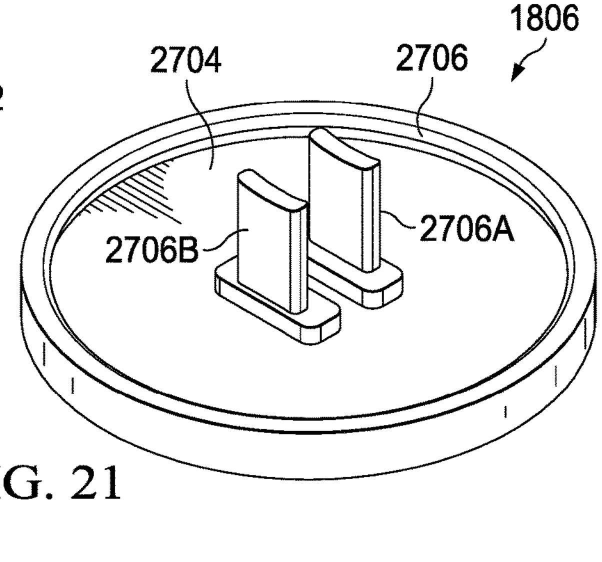
FIG. 21 is an isometric view of a preferred assembly tower.

Referring to FIG. 21, anchor assembly tower 1806 will be further described.

Anchor assembly tower 1806 forms a generally flat cylindrical cap with base surface 2704. Rising from base surface 2704 is annular detent ring 2706. Annular detent ring 2706 is adapted to removably engage detent blocking ring 2502 of the sliding cartridge, as will be further described.

The interior surface of base surface 2704 further supports vertical cap support stanchion 2706A and vertical cap support stanchion 2706B. In a preferred embodiment, the cap support stanchions are diametrically opposed and perpendicular to base 2704. The cap support stanchions are adapted to engage lower surfaces of the anchor cap to stabilize the lead anchor assembly before use, as will be further described.

Figure 22:
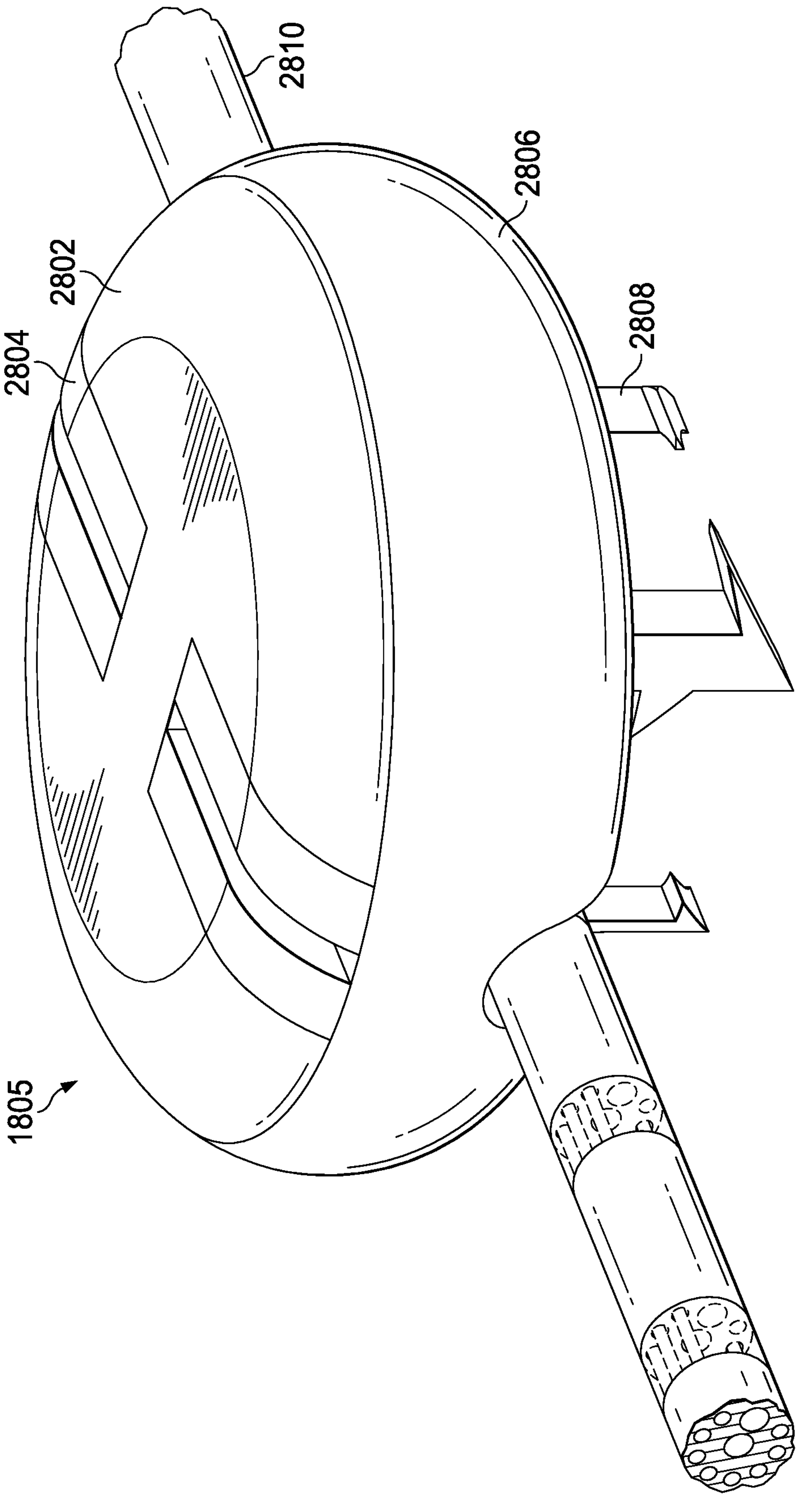
FIG. 22 is an isometric view of a preferred lead anchor assembly.
Figure 23:
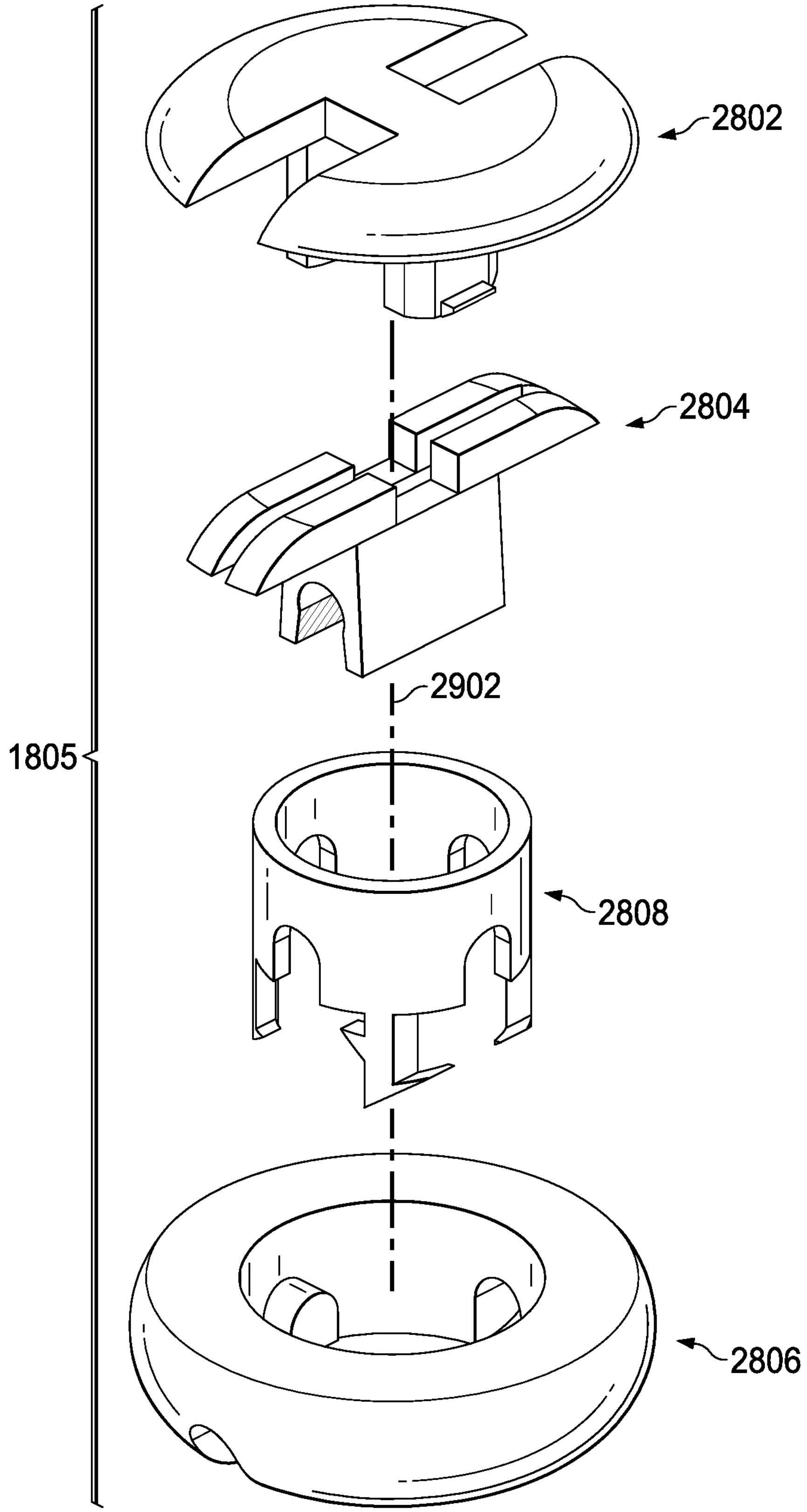
FIG. 23 is an exploded isometric view of a preferred lead anchor assembly.
Figure 24:
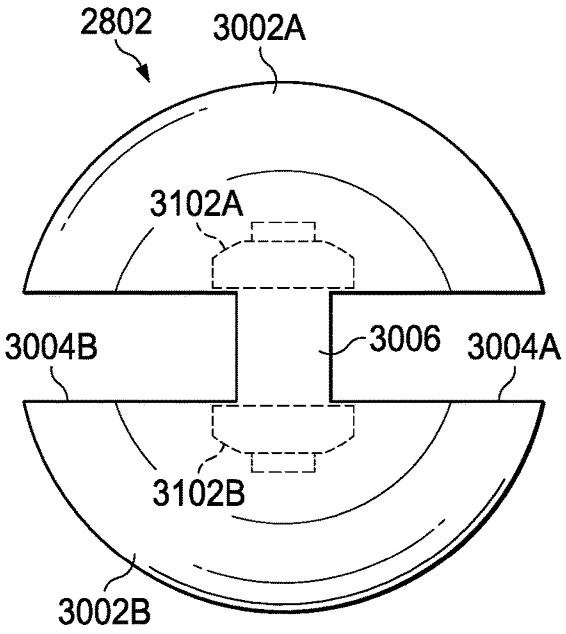
FIG. 24 is a top view of a preferred anchor cap.
Figure 25:
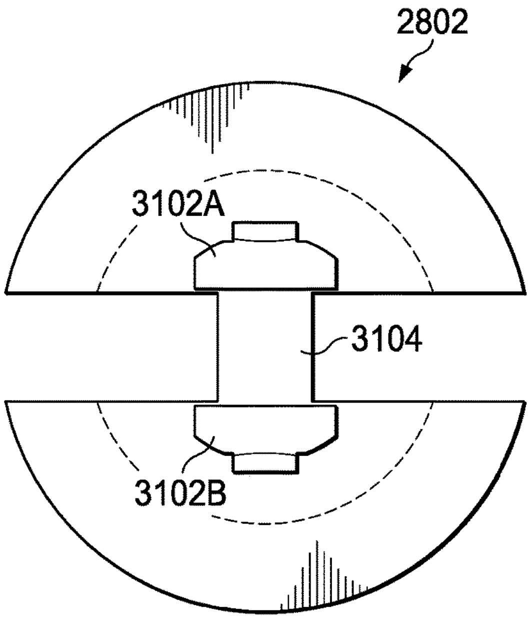
FIG. 25 is a bottom view of a preferred anchor cap.
Figure 26:
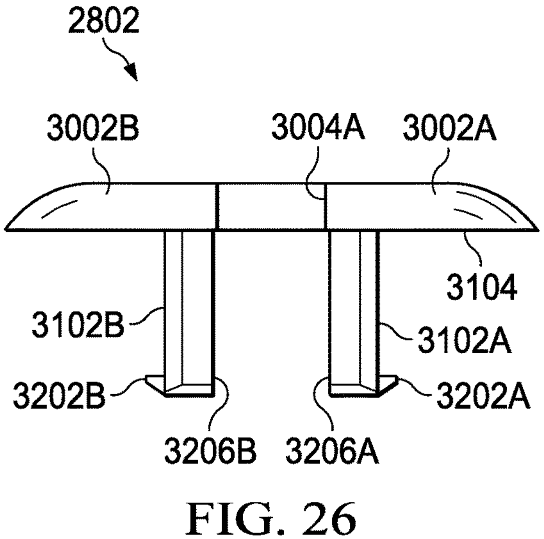
FIG. 26 is a side view of a preferred anchor cap.
Figure 27:
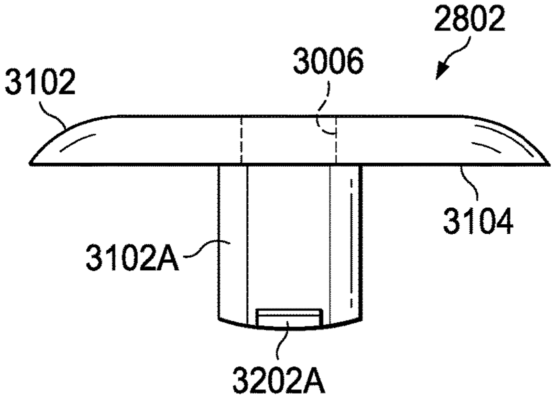
FIG. 27 is a side view of a preferred anchor cap.

Referring to FIGS. 22 and 23, lead anchor assembly 1805 will be further described.

Lead anchor assembly is further comprised of anchor cap 2802, lead stabilizer 2804, barbed tube 2808, and toroid 2806. Anchor cap 2802, lead stabilizer 2804, barbed tube 2808, and toroid 2806, in a preferred embodiment, are coaxially arranged about central axis 2902. Central axis 2902 is co-linear with the longitudinal central axis of the lead anchor and deployment tool. When assembled, lead stabilizer 2804 grips percutaneous lead 2810 and prevents it from moving with respect to the assembly.

Referring to FIGS. 24, 25, 26, and 27, anchor cap 2802 will be further described. Anchor cap 2802 generally comprises two semicircular plates, 3002A and 3002B, joined by central web 3006. Semicircular plates 3002A and 3002B are separated by stabilizer receiver slots 3004A and 3004B. Semicircular plate 3002A, semicircular plate 3002B and web 3006 share base surface 3104. Lock stanchion 3102A and lock stanchion 3102B are integrally formed with and extend downwardly from base surface 3104, and adjacent web 3006. In a preferred embodiment, the lock stanchions are diametrically opposed and adapted to extend between the lead stabilizer and the barbed tube.

Lock stanchion 3102A further comprises outwardly facing locking tab 3202A. Likewise, lock stanchion 3102B further comprises outwardly facing locking tab 3202B. The locking tabs are adapted to engage the toroid. Lock stanchion 3102A further comprises inwardly facing pressure surface 3206A. Likewise, lock stanchion 3102B further comprises inwardly facing pressure surface 3206B. In a preferred embodiment, pressure surface 3206A and pressure surface 3206B are parallel with each other and with axis 2902. In a preferred embodiment, anchor cap 2802 is comprised of a flexible plastic such as polypropylene, Teflon or Delrin.

Figure 28:
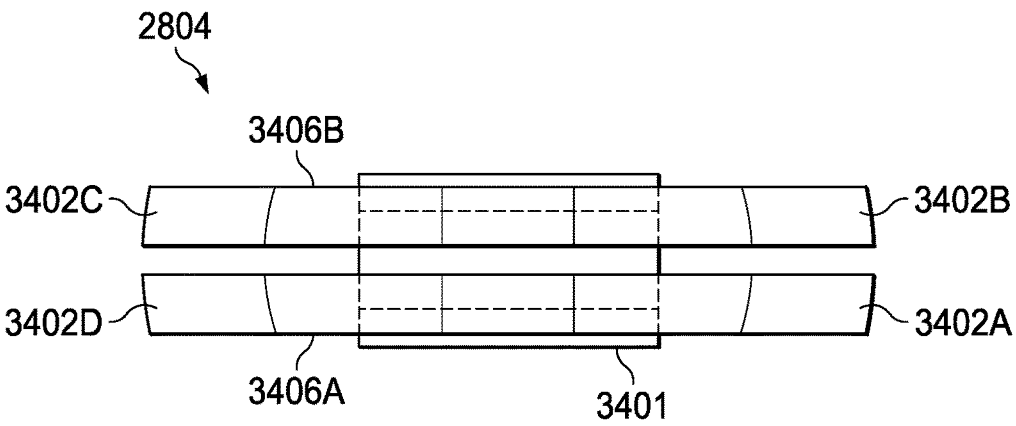
FIG. 28 is a top view of a preferred lead stabilizer.
Figure 29:
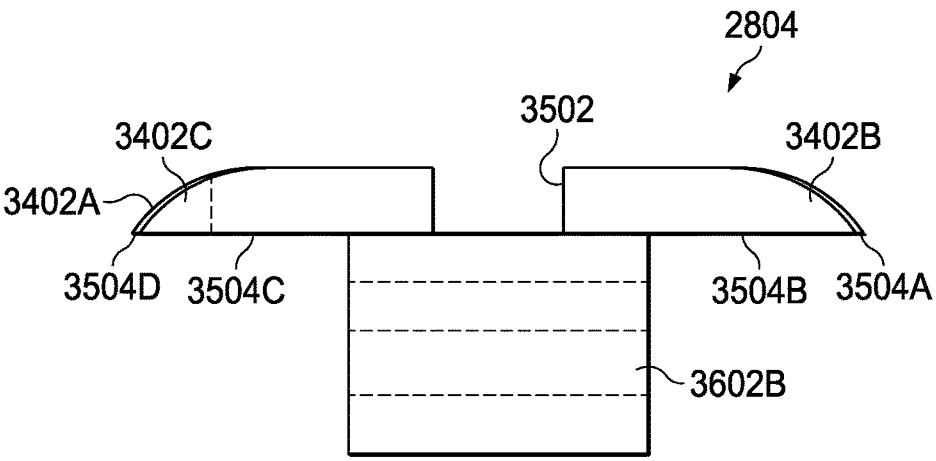
FIG. 29 is a side view of a preferred lead stabilizer.
Figure 30:
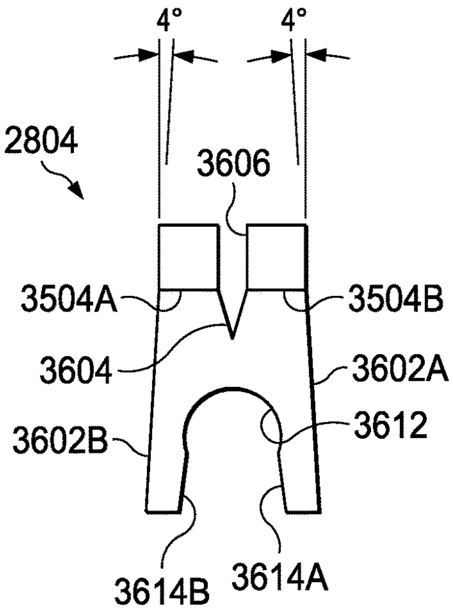
FIG. 30 is a side view of a preferred lead stabilizer.
Figure 31:
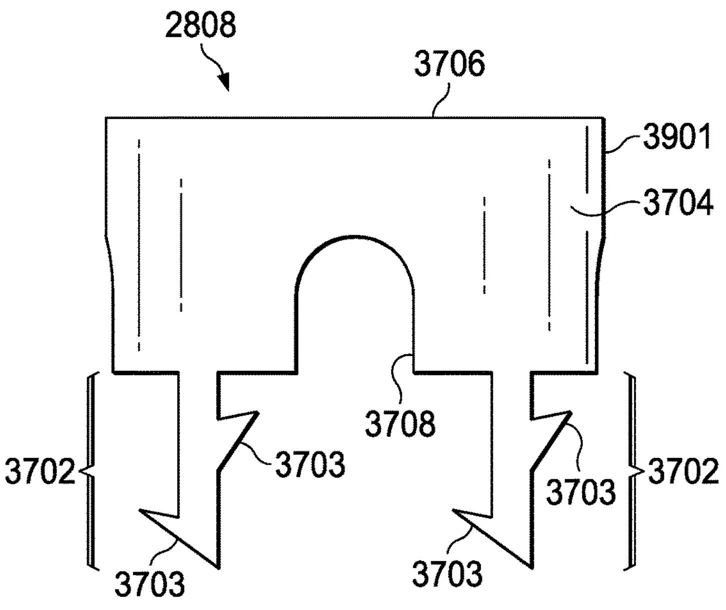
FIG. 31 is a side view of a preferred barbed tube.
Figure 32:
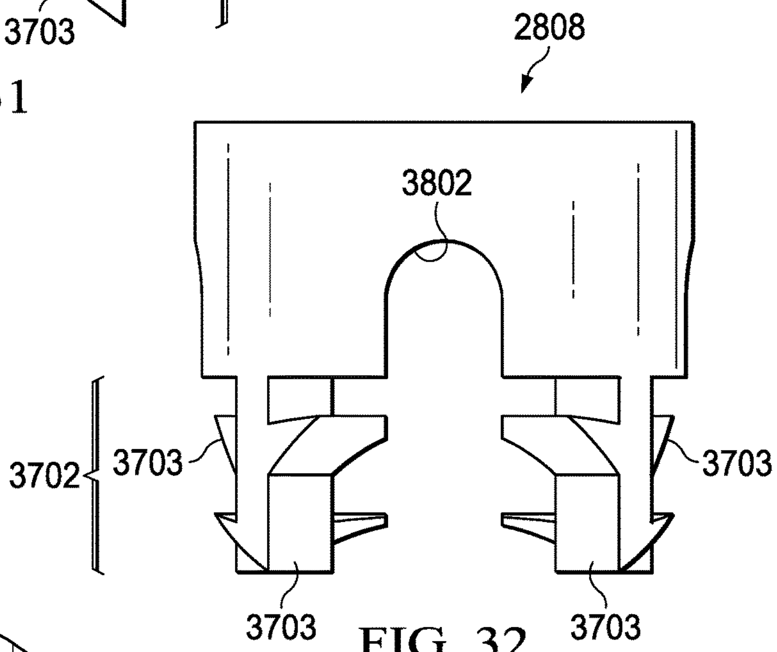
FIG. 32 is a side view of a preferred barbed tube.
Figure 33:
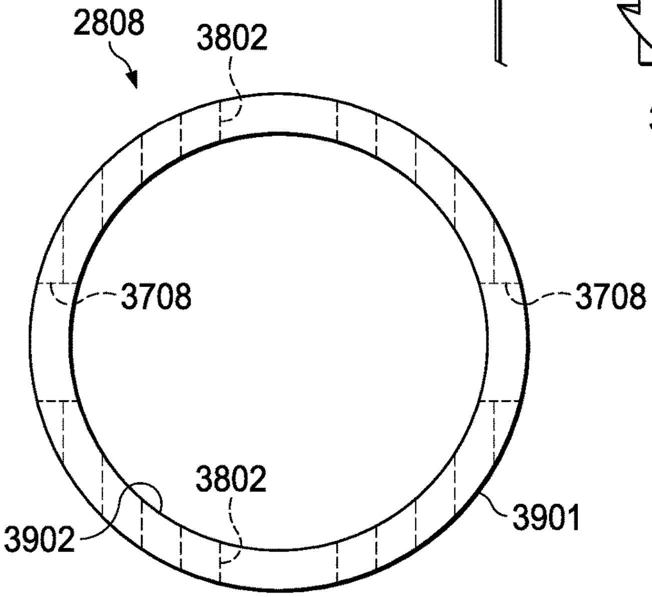
FIG. 33 is a top view of a preferred barbed tube.

Referred to FIGS. 28, 29, and 30, lead stabilizer 2804 will be further described.

Lead stabilizer 2804 is generally "T-shaped" and is comprised of a flexible, yet resilient plastic, such as nylon or Delrin.

Lead stabilizer 2804 is comprised of stabilizer body 3401. Stabilizer body 3401 supports two generally horizontal retainer arms 3406A and 3406B.

Retainer arm 3406B is defined by arcuate surface 3402A and arcuate surface 3402D. Likewise, retainer arm 3406B is defined by arcuate surface 3402B and arcuate surface 3402C. Retainer arm 3406A is further defined by base surface 3504A, opposite arcuate surface 3402A, and base surface 3504D, opposite arcuate surface 3402D. Likewise, retainer arm 3406B is further defined by base surface 3504B opposite arcuate surface 3402B, and base surface 3504C opposite arcuate surface 3402C. Retainer arm 3406A and retainer arm 3406B are separated by latitudinal access groove 3606. Both retainer arms are further separated by cap receiver slot 3502 which is adapted to accept web 3006. Access groove 3606 terminates in latitudinal living hinge 3604, within stabilizer body 3401.

Stabilizer body 3401 is further defined by downwardly-oriented stabilizer arm 3602A and downwardly-oriented stabilizer arm 3602B. Stabilizer arm 3602A preferably is formed at about a 4° angle with respect to axis 2902. Likewise, stabilizer arm 3602B is preferably formed at about a 4° angle with axis 2902. Stabilizer arm 3602A and stabilizer arm 3602B are separated by lead receiver surface 3612. Lead receiver surface 3612 is generally latitudinal and positioned parallel with and below access groove 3606. In a preferred embodiment, lead receiver surface 3612 is generally semi-cylindrical and adapted to fit or be slightly smaller than the diameter of percutaneous lead 2810.

Lead receiver surface 3612 is bounded by lead guide surface 3614A and lead guide surface 3614B. Lead guide surface 3614B is generally parallel with stabilizer arm 3602A. Lead guide surface 3614B is generally parallel with stabilizer arm 3602B. In a preferred embodiment, both lead guide surface 3614A and lead guide surface 3614B include a surface pattern to increase friction with percutaneous lead 2810.

Referring to FIGS. 31, 32, 33 and 34, barbed tube 2808 will be further described.

Barbed tube 2808 is comprised of tube body 3704. Tube body 3704 is generally cylindrical and adapted to fit within toroid 2806 and around lead stabilizer 2804. Tube body 3704 includes cylindrical interior surface 3902 and cylindrical exterior surface 3901. Tube body 3704 further includes upward-facing contact surface 3706.

Tube body 3704 further comprises lead channel 3708 and locking channel 3802. In a preferred embodiment, lead channel 3708 spans the diameter of tube body 3704. Likewise locking channel 3802 spans the diameter of tube body 3704. In a preferred embodiment, locking channel 3802 is disposed at 90° with respect to lead channel 3708. Tube body 3704 further comprises four (4) downwardly disposed anchor hooks 3702. Each downwardly disposed anchor hook 3702 includes one or more tines 3703. Importantly, the anchor hooks and the tines share interior surface 3902 and exterior surface 3901.

In a preferred embodiment, barbed tube 2808 is comprised of titanium, a suitable titanium alloy or stainless steel.

Figure 35:
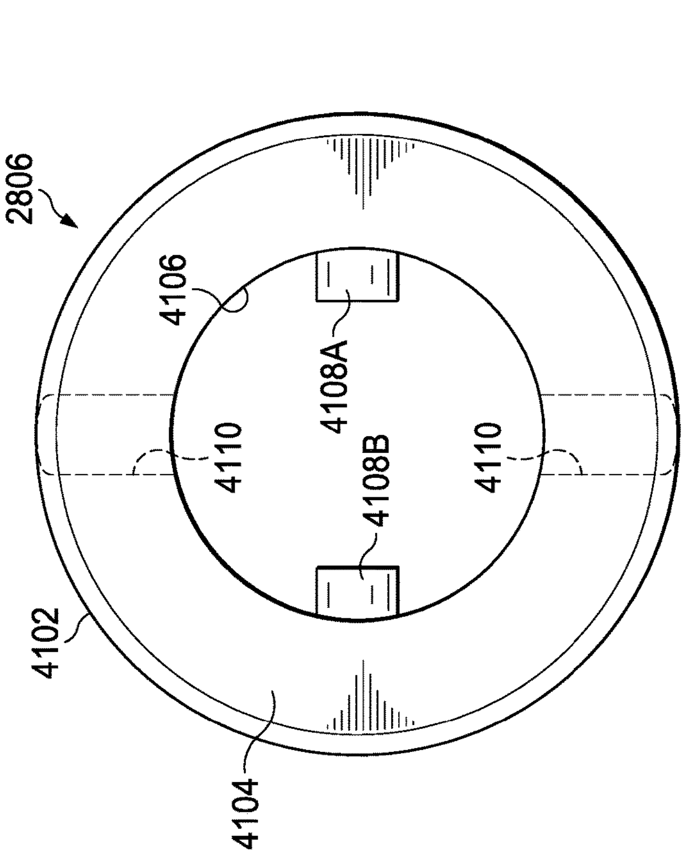
FIG. 35 is a top view of a preferred toroid.
Figure 37:
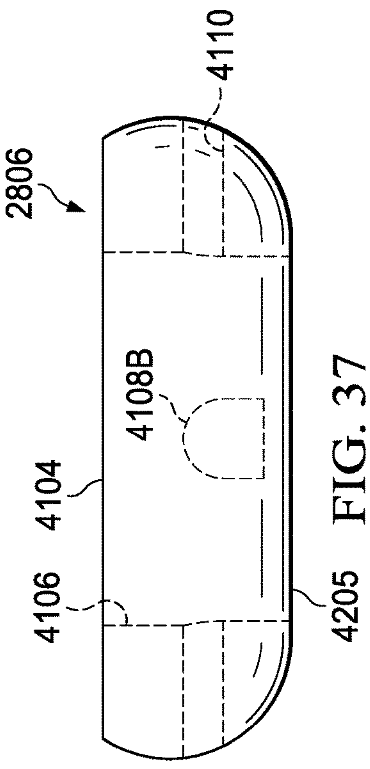
FIG. 37 is a side view of a preferred toroid.
Figure 34:
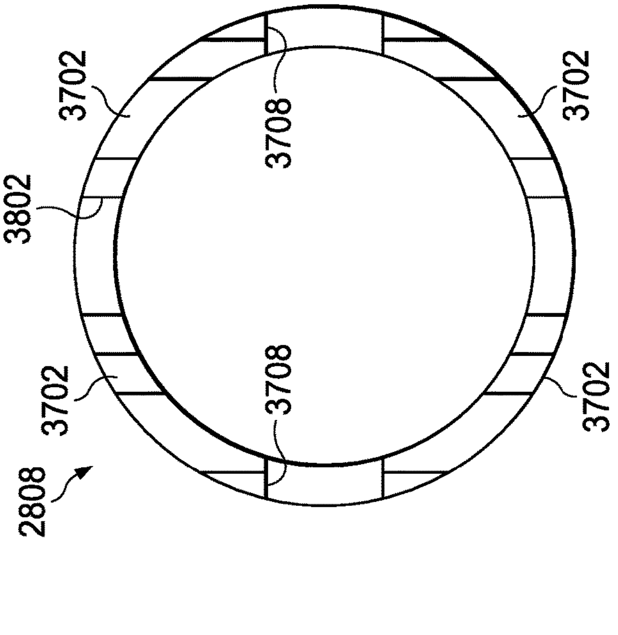
FIG. 34 is a bottom view of a preferred barbed tube.
Figure 36:
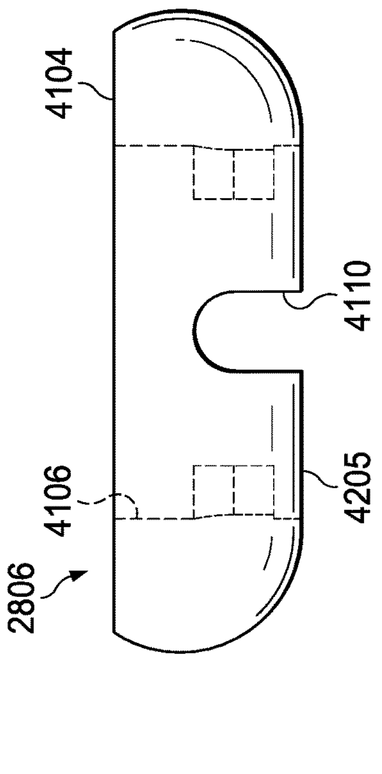
FIG. 36 is a side view of a preferred toroid.

Referring to FIGS. 35, 36 and 37, toroid 2806 will be further described.

Toroid 2806 is comprised of toroid body 4102. Toroid body 4102 is generally toroidal in shape, yet having a flat upper contact surface 4104 and a flat lower contact surface 4205. In a preferred embodiment, upper contact surface 4104 and lower contact surface 4205 are generally parallel.

Toroid body 4102 further comprises cylindrical interior surface 4106. Cylindrical interior surface 4106 is generally adapted to receive and constrict the exterior surface of barbed tube 2808, as will be further described.

Cylindrical interior surface 4106 further includes barbed tube positioning bar 4108A and barbed tube positioning bar 4108B. Barbed tube positioning bar 4108A and barbed tube positioning bar 4108B are diametrically opposed and adapted to fit within locking channel 3802 of the barbed tube.

Toroid body 4102 is further comprised of lead channel 4110. Lead channel 4110, in a preferred embodiment, diametrically spans the toroid and is adapted to fit the exterior surface of percutaneous lead 2810. In a preferred embodiment, lead channel 4110 is disposed within toroid body 4102 at a 90° angle with respect to barbed tube positioning bars 4108A and 4108B.

In a preferred embodiment, toroid 2806 is comprised of polycarbonate or similar plastic, but alternatively may be titanium, a titanium alloy or stainless steel.

Figure 38:
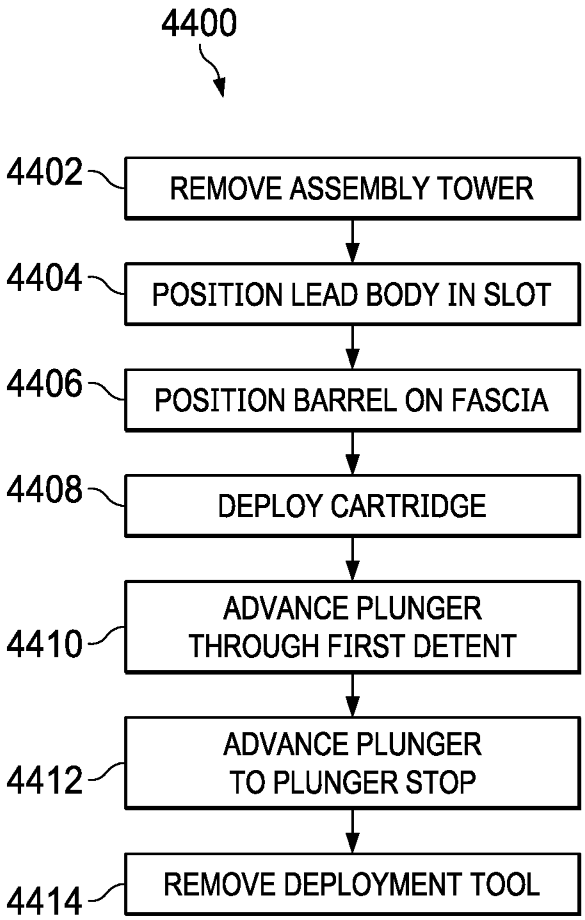
FIG. 38 is a flowchart of a preferred method of use of the lead anchor and deployment tool.

Referring to FIG. 38, method 4400 of use of lead anchor and deployment tool 1800 will be further described.

In a preferred embodiment, the lead anchor and deployment tool are preassembled with plunger 1802 within barrel 1804 and lead anchor assembly 1805 positioned within bay 1930. Assembly tower 1806 is positioned at the distal end of sliding cartridge 1807 and is held in place frictionally by detent ring 2706 engaging detent blocking ring 2502. Cap support stanchion 2706A and cap support stanchion 2706B are positioned upwardly within the lead anchor assembly and engage locking tab 3202A and locking tab 3202B. Anchor cap 2802 is thereby held in position adjacent to and above lead stabilizer 2804 and barbed tube 2808. In this position, cap support stanchion 2706A and cap support stanchion 2706B are adjacent interior surface 3902 of barbed tube 2808 and adjacent to stabilizer arm 3602A and stabilizer arm 3602B of lead stabilizer 2804. Also in this position, cap deployment arm 2222A and cap deployment arm 2222B of plunger 1802 are in contact with semicircular plates 3002A and 3002B of anchor cap 2802.

At step 4402, the assembly tower is removed from the sliding cartridge by disengaging detent ring 2706 from detent blocking ring 2502 and discarded.

At step 4404, percutaneous lead 2810 is positioned within lead channel 4110 of toroid 2806 and lead channel 2404 of sliding cartridge 1807.

At step 4406, the lead anchor deployment tool is positioned in a preferred location on the fascia.

At step 4408, barrel 1804 is advanced downwardly toward the fascia thereby forcing cartridge 1807 onto the fascia and upwardly in cartridge guides 1919A and 1919B. Cartridge guide receivers 2408A and 2408B of the sliding cartridge constrain movement of the cartridge upward and coaxial with the longitudinal axis of the lead anchor and deployment tool. As sliding cartridge 1807 moves upward on barrel 1804, compressor deployment arm 1920A and compressor deployment arm 1920B of the barrel force lead stabilizer 2804 downwardly until the base surfaces of the lead stabilizer engage contact surface 3706 of the barbed tube. Such engagement forces barbed tube 2808 downward into cylindrical interior surface 4106 of toroid 2806. Further, forcing barrel 1804 downward with respect to cartridge 1807 forces percutaneous lead 2810 upward into lead guide surfaces 3614A and 3614B of lead stabilizer 2804 and into lead receiver surface 3612. Simultaneously, anchor hooks 3702 of barbed tube 2808 puncture the fascia. Tines 3703 hold the barbed tube in place at the preferred location in the fascia.

In this position, percutaneous lead 2810 may still move axially within lead receiver surface 3612 of lead stabilizer 2804.

At step 4410, plunger 1802 is advanced past detent ring 2306 thereby deforming detent blocking ring 1914 sufficiently to allow passage. Advancing the plunger past detent ring 2306 moves anchor cap 2802 downward toward lead stabilizer 2804, thereby positioning pressure surfaces 3206A and 3206B of anchor cap 2802 adjacent stabilizer arms 3602A and 3602B of lead stabilizer 2804.

At step 4412, the plunger is advanced to plunger stop 1915 of barrel 1804. In this position, locking tabs 3202A and 3202B of anchor cap 2802 expand under and become fixed to lower contact surface 4205 of toroid 2806. Simultaneously, locking stanchions 3102A and 3102B compress stabilizer arms 3602A and 3602B inwardly by approximately 4° each. This inward pressure activates living hinge 3604 and moves guide surfaces 3614A and 3614B inwardly thereby constricting the movement of percutaneous lead 2810.

Simultaneously, locking channel 3802 of barbed tube 2808 is positioned adjacent barbed tube positioning bar 4108A and barbed tube positioning bar 4108B of toroid 2806, thereby preventing rotation of barbed tube 2808 with respect to toroid 2806. In this position, barbed tube 2808 is further constrained from upward axial movement by engagement of the base surface of the lead stabilizer and the base surface of the anchor cap with contact surface 3706 of the blocking ring. Barbed tube 2808 is further constrained from downward axial movement by engagement of locking channel 3802 of the barbed tube with barbed tube positioning bars 4108A and 4108B of the toroid.

Retainer arm 3406A and retainer arm 3406B are frictionally engaged with stabilizer receiver slot 3004A and 3004B of anchor cap 2802, thereby further stabilizing lead stabilizer 2804 within anchor cap 2802.

At step 4414, the plunger, barrel and sliding cartridge are removed and discarded, leaving lead anchor assembly 1805 fixed in the fascia securing percutaneous lead 2810.

The invention claimed is:

1. An anchor device configured to anchor an electrode lead to a fascia, the electrode lead configured to deliver electrical stimulation to a patient, the anchor device comprising:

an anchor body, having a longitudinal passage;

a first latitudinal lead channel formed in the anchor body;

a barbed tube, positioned in the longitudinal passage, having a downwardly oriented set of anchor hooks;

a lead stabilizer, positioned in the barbed tube, having a second latitudinal lead channel;

an anchor cap, positioned adjacent the barbed tube and the second latitudinal lead channel; and wherein the anchor cap compresses the second latitudinal lead channel;

wherein the downwardly orientated set of anchor hooks protrude out of the longitudinal passage away from the anchor body and penetrate the fascia.

2. The anchor device of claim 1 wherein the lead stabilizer further comprises a set of stabilizer arms adjacent the second latitudinal lead channel.

3. The anchor device of claim 2 wherein the lead stabilizer further comprises:

a set of retainer arms, adjacent the anchor cap, separated by an access groove; and a living hinge adjacent the access groove and the second latitudinal lead channel.

4. The anchor device of claim 3 wherein the anchor cap further comprises a set of lock stanchions which directly abuts the set of retainer arms.

5. The anchor device of claim 3 wherein the anchor cap further comprises a stabilizer receiver slot which directly abuts the set of retainer arms.

6. The anchor device of claim 1 wherein the barbed tube further comprises:

a generally cylindrical tube body; and a third latitudinal lead channel, colinear with the first latitudinal lead channel and with the second latitudinal lead channel, in the generally cylindrical tube body.

7. The anchor device of claim 6 wherein:

the anchor body further comprises a set of inwardly projecting radial positioning bars in the longitudinal passage; and a locking channel, adjacent the set of inwardly projecting radial positioning bars, formed in the generally cylindrical tube body.

8. The anchor device of claim 6 wherein the set of anchor hooks further comprises a set of tines, formed in the tube body.

9. The anchor device of claim 6 wherein:

the electrode lead is positioned in the first latitudinal lead channel, the second latitudinal lead channel and the third latitudinal lead channel.

10. The anchor device of claim 1 wherein the anchor body is generally toroidal.

11. The anchor device of claim 1 wherein the lead stabilizer is formed of a semi-rigid plastic.

12. A system for implanting an anchoring device for a percutaneous lead for an electrode in a fascia, the system comprising:

a barrel, having an external surface, an internal surface and a storage bay;

a plunger, slidingly disposed adjacent the internal surface, and adjacent the storage bay;

a cartridge, slidingly disposed on the external surface;

a lead anchor assembly, having a distal end; and a removable lower cap, directly abutting and releasably connected to the cartridge and directly abutting and releasably connected to the lead anchor assembly, at the distal end.

13. The system of claim 12 further comprising an assembly tower, removably attached to the cartridge and engaging the lead anchor assembly.

14. The system of claim 12 wherein:

advancing the cartridge along the barrel moves the lead anchor assembly into the storage bay and deploys a set of hooks on the lead anchor assembly; and depressing the plunger in the barrel fixes the percutaneous lead in the lead anchor assembly.

15. The system of claim 12 wherein the cartridge further comprises:

a first latitudinal lead anchor channel; and the lead anchor assembly further comprises a second latitudinal lead anchor channel, aligned with the first latitudinal lead anchor channel.

16. The system of claim 12:

wherein the plunger further comprises a first detent and a second detent;

wherein the barrel further comprises a third detent and a plunger stop; and wherein the plunger engages the lead anchor assembly when the first detent contacts the third detent;

wherein the percutaneous lead is secured in the lead anchor assembly when the second detent contacts the plunger stop.

17. A method of implanting a lead anchor assembly for an electrode lead in a fascia comprising the steps of:

providing a barrel, having an external surface, an internal surface and a storage bay;

providing a plunger, slidingly disposed adjacent the internal surface, and adjacent the storage bay;

providing a cartridge, slidingly disposed on the external surface;

providing a removable lower cap;

providing the lead anchor assembly, with a distal end and a lead channel, directly abutting and releasably connected to the cartridge and directly abutting and releasably connected to the removable lower cap at the distal end;

positioning the electrode lead in the lead channel;

positioning the barrel on the fascia;

depressing the barrel toward the fascia, thereby advancing the cartridge on the barrel and deploying a set of hooks on the lead anchor assembly into the fascia; and depressing the plunger toward the barrel thereby fixing the electrode lead in the lead anchor assembly.

18. The method of claim 17 further comprising the step of:

removing the barrel from the lead anchor assembly.

* * * * *